US012329487B2

(12) United States Patent
Thompson et al.

(10) Patent No.: US 12,329,487 B2
(45) Date of Patent: Jun. 17, 2025

(54) MASTER CONTROL DEVICE WITH FINGER GRIP SENSING AND METHODS THEREFOR

(71) Applicant: Intuitive Surgical Operations, Inc., Sunnyvale, CA (US)

(72) Inventors: Allen C. Thompson, Los Altos, CA (US); Salvatore J. Brogna, Los Gatos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1226 days.

(21) Appl. No.: 17/054,109

(22) PCT Filed: May 10, 2019

(86) PCT No.: PCT/US2019/031813
§ 371 (c)(1),
(2) Date: Nov. 9, 2020

(87) PCT Pub. No.: WO2019/217882
PCT Pub. Date: Nov. 14, 2019

(65) Prior Publication Data
US 2021/0298855 A1    Sep. 30, 2021

Related U.S. Application Data

(60) Provisional application No. 62/669,991, filed on May 11, 2018.

(51) Int. Cl.
*A61B 5/026*      (2006.01)
*A61B 34/00*      (2016.01)
(Continued)

(52) U.S. Cl.
CPC .............. *A61B 34/74* (2016.02); *A61B 34/35* (2016.02); *A61B 2090/064* (2016.02)

(58) Field of Classification Search
CPC .................................................... A61M 27/00
See application file for complete search history.

(56) References Cited

U.S. PATENT DOCUMENTS

| 3,350,956 A | 11/1967 | Barton et al. |
| 5,176,696 A | 1/1993 | Saunders |
| (Continued) | | |

FOREIGN PATENT DOCUMENTS

| EP | 3015081 A1 | 5/2016 |
| EP | 3245975 A1 | 11/2017 |
| (Continued) | | |

OTHER PUBLICATIONS

International Search Report and Written Opinion for Application No. PCT/US2018/061031, mailed on Apr. 15, 2019, 19 pages.

(Continued)

*Primary Examiner* — Kawing Chan
*Assistant Examiner* — Charles S Laughlin
(74) *Attorney, Agent, or Firm* — IP Spring

(57) ABSTRACT

Implementations relate to a master control device and methods for using such a control device. In some implementations, a master control device includes a control body including a surface. A force sensor is coupled to the control body, the force sensor configured to sense forces applied to the surface of the control body and provide sensor signals in accordance with amounts of the forces received on sides of the control body caused by a pinching of the control body between fingers of a user. At least one sensor is configured to detect at least one of a position and an orientation of the control body in a working environment of the control body.

20 Claims, 10 Drawing Sheets

(51) Int. Cl.
*A61B 34/35* (2016.01)
*A61B 90/00* (2016.01)

(56) References Cited

U.S. PATENT DOCUMENTS

| | | | |
|---|---|---|---|
| 5,410,638 | A | 4/1995 | Colgate et al. |
| 5,876,325 | A | 3/1999 | Mizuno et al. |
| 5,976,121 | A | 11/1999 | Matern et al. |
| 6,089,106 | A * | 7/2000 | Patel ................. B60R 21/01516 177/144 |
| 8,016,818 | B2 | 9/2011 | Ellis et al. |
| 8,521,331 | B2 | 8/2013 | Itkowitz |
| 8,638,057 | B2 | 1/2014 | Goldberg et al. |
| 2008/0262538 | A1 | 10/2008 | Danitz et al. |
| 2009/0030428 | A1 | 1/2009 | Omori et al. |
| 2010/0069940 | A1 | 3/2010 | Miller et al. |
| 2010/0080669 | A1 | 4/2010 | Labonville et al. |
| 2010/0228156 | A1 | 9/2010 | Valero-Cuevas et al. |
| 2011/0118753 | A1 | 5/2011 | Itkowitz et al. |
| 2011/0208000 | A1* | 8/2011 | Honda ................. A61B 1/0016 600/118 |
| 2012/0041595 | A1 | 2/2012 | Greeley et al. |
| 2013/0035697 | A1 | 2/2013 | Ogawa et al. |
| 2014/0018960 | A1 | 1/2014 | Itkowitz |
| 2014/0160015 | A1 | 6/2014 | Ogawa et al. |
| 2014/0165770 | A1 | 6/2014 | Abri et al. |
| 2014/0276646 | A1 | 9/2014 | Wong et al. |
| 2015/0073340 | A1 | 3/2015 | Pacheco et al. |
| 2015/0290814 | A1 | 10/2015 | Schiele et al. |
| 2016/0202134 | A1 | 7/2016 | Malackowski et al. |
| 2016/0216167 | A1 | 7/2016 | Blumenkranz et al. |
| 2017/0095298 | A1 | 4/2017 | Vakharia et al. |
| 2017/0296280 | A1 | 10/2017 | Ogawa et al. |
| 2018/0168758 | A1 | 6/2018 | Lutzow et al. |
| 2020/0275985 | A1 | 9/2020 | Thompson et al. |
| 2020/0289216 | A1* | 9/2020 | Denlinger ............. A61B 34/37 |
| 2020/0390510 | A1 | 12/2020 | Thompson et al. |

FOREIGN PATENT DOCUMENTS

| | | |
|---|---|---|
| JP | 2006321027 A | 11/2006 |
| WO | WO-2012127404 A2 | 9/2012 |
| WO | WO-2013018933 A1 | 2/2013 |
| WO | WO-2016154173 A1 | 9/2016 |
| WO | WO-2016201544 A1 | 12/2016 |
| WO | WO-2017031132 A1 | 2/2017 |
| WO | WO-2019099504 A1 | 5/2019 |
| WO | WO-2019099584 A1 | 5/2019 |

OTHER PUBLICATIONS

International Search Report and Written Opinion for Application No. PCT/US2018/061143, mailed on Apr. 15, 2019, 22 pages.
International Search Report and Written Opinion for Application No. PCT/US2019/031813, mailed on Aug. 14, 2019, 13 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Preliminary Report on Patentability for Application No. PCT/US2018/061031, mailed on May 19, 2020, 13 pages.
International Preliminary Report on Patentability for Application No. PCT/US2018/061143, mailed on May 28, 2020, 15 pages.
Extended European Search Report for Application No. EP18878247.8 mailed on Jul. 9, 2021. 10 pages.
Extended European Search Report for Application No. EP18879759.1, mailed on Nov. 11, 2021, 13 pages.
International Preliminary Report on Patentability for Application No. PCT/US2019/031813, mailed on Nov. 26, 2020, 10 pages.

* cited by examiner

MASTER CONTROL DEVICE WITH FINGER GRIP SENSING AND METHODS THEREFOR

CROSS-REFERENCE TO RELATED APPLICATIONS

The present application is a U.S. National Phase application of International Patent Application No. PCT/US2019/031813, filed May 10, 2019 and titled "Master Control Device with Finger Grip Sensing and Methods Therefor," which claims priority to U.S. Provisional Patent Application No. 62/669,991, filed May 11, 2018 and titled "Master Control Device with Finger Grip Sensing and Methods Therefor," the entire contents of both of which are hereby incorporated by reference.

BACKGROUND

In teleoperated operations such as teleoperated surgery, a user typically operates a master controller, e.g., included in a workstation or console, to remotely control (e.g., teleoperate) the motion and functions of instruments at a work site (e.g., surgical site). The master controller utilizes master controls, which will typically include one or more hand input devices such as pincher grips, joysticks, exo-skeletal gloves, or the like. These hand input devices are in communication with the controlled instrument. More specifically, a manipulator or "slave" device including the instrument is moved based on the user's manipulation of the hand input devices. In some examples of a surgical or other medical operation, a hand input device may control, via the teleoperated surgery system, a variety of surgical instruments such as tissue graspers, needle drivers, electrosurgical cautery probes, etc. Each of these instruments performs functions for the surgeon, for example, holding or driving a needle, grasping a blood vessel, or dissecting, cauterizing, or coagulating tissue.

For some hand input devices, the user may have difficulty manipulating the hand input device, e.g., over long periods of time, while maintaining a secure grip on the hand input device. Further, in some situations, it may be beneficial to operate the hand input device without being bound to a stationary workstation or console.

SUMMARY

Implementations of the present application relate to a master control device and methods for using such a control device. In some implementations, a master control device includes an elongated control body including a surface. A force sensor is coupled to the elongated control body, the force sensor configured to sense forces applied to the surface of the elongated control body and provide sensor signals in accordance with amounts of the forces received on sides of the elongated control body caused by a pinching of the elongated control body between fingers of a user. At least one sensor is configured to detect at least one of a position and an orientation of the elongated control body in a working environment of the elongated control body.

Various implementations and examples of the master control device are described. For example, in some implementations, the master control device is a surgical system master control device configured to provide control signals to a surgical teleoperated system. In some implementations, the surface of the elongated control body includes deformable portions that are configured to deform from the forces received on the sides of the elongated control body, and the force sensor is configured to sense the deformation. In some implementations, a fluid is provided within a housing of the elongated control body, and the force sensor includes a transducer configured to detect deformation of the deformable portions of the surface by detecting fluid pressure in response to the deformation. For example, the fluid can be a gas or a liquid. In some implementations, a rib structure is provided within the elongated control body, where the rib structure is more rigid than a structure of the deformable portions of the elongated control body. Some implementations include a spine shaft extending along a lengthwise axis of the elongated control body, where the spine shaft is more rigid than a structure of the deformable portions of the elongated control body. In some examples, the rib structure includes ribs provided in a helix centered around the spine shaft. In some examples, one or more ribs of the ribs structure have a bend in their cross-sectional length from the spine shaft to a wall of the elongated control body, where the one or more ribs are configured to buckle in a particular direction in response to a threshold force causing the deformation of the deformable portions of the elongated control body.

In some examples, the force sensor includes a strain gauge. In some implementations, the force sensor includes a force-sensing film coupled to the surface of the elongated control body, where the force-sensing film receives the forces from one or more fingers of the user. In some implementations, the force sensor includes one or more force-sensitive elements that are positioned to receive the forces applied to the surface of the elongated control body, the force-sensitive elements opposing deformation by the forces received on opposite sides of the elongated control body.

Some implementations provide an elongated control body that is axisymmetric about a lengthwise axis extending through the elongated control body. In some implementations, the master control device includes an input control coupled to the elongated control body and configured to output a control signal in response to being activated by a finger of the user. In some examples, the input control includes a button or a switch. In some implementations, the elongated control body includes a physical feature corresponding to a controller control point, where the controller control point corresponds to an instrument control point of a slave instrument controlled by the surgical system master control device. For example, the physical feature can include at least one of a ring, a bump, a divot, and a bulge on the surface of the elongated control body. In some implementations, the elongated control body is mechanically ungrounded. In some implementations, the control body is coupled to a mechanically grounded linkage.

In some implementations, a master control device includes a control body configured to engage fingers of a hand of a user, where the control body includes a surface that is deformable at a plurality of deformable portions of the surface. A force sensor is coupled to the control body and is configured to sense forces applied to the plurality of deformable portions of the surface of the control body from one or more of the fingers of the user, the forces causing a deformation of the plurality of deformable portions of the surface. The force sensor is configured to provide sensor signals in accordance with the deformation of the plurality of deformable portions of the surface. The master control device includes at least one sensor configured to detect a position and an orientation of the control body in a working environment of the control body.

Various implementations and examples of the master control device are described. In some implementations, the control body is elongated and at least partially cylindrical. In some implementations, the surface of the control body is spherical. In some examples, the forces are caused by a pinching of the control body between the fingers. Some implementations further include a fluid provided within a housing of the control body, where the force sensor includes a force transducer configured to detect pressure in the fluid caused by deformation of the plurality of deformable portions of the surface.

In some implementations, a rib structure is provided within the control body, where the rib structure is more rigid than a wall of a housing of the control body that is configured to be gripped by the fingers of the user. Some implementations include a spine shaft extending along a lengthwise axis of the control body, where the spine shaft is more rigid than a wall of a housing of the control body that is configured to be gripped by the fingers of the user. In some examples, the rib structure includes ribs provided in a helix centered around the spine shaft.

Some implementations provide a control body that is axisymmetric about a lengthwise axis extending through the control body. In some implementations, the master control device includes an input control coupled to the control body and configured to output a control signal in response to being activated by a finger of the user. In some implementations, the control body includes a physical feature corresponding to a controller control point, where the controller control point corresponds to an instrument control point of a slave instrument controlled by the master control device. In some examples, the physical feature includes a ring, a bump, a divot, and/or a bulge on the surface of the control body, and/or a region having a different physical texture than surrounding surfaces. In various implementations, the control body is mechanically ungrounded, or is coupled to a mechanically grounded linkage.

In some implementations, a master control system includes a master device that includes an elongated control body including a surface configured to engage fingers of a hand of a user; at least one sensor configured to detect a position and an orientation of the elongated control body in a working environment of the elongated control body; and a force sensor coupled to the elongated control body, the force sensor configured to sense forces applied to the surface of the elongated control body and provide sensor signals in accordance with amounts of the forces received on opposite sides of the elongated control body. The master control system includes a controller coupled to a slave surgical device and in communication with the master device, where the controller is configured to provide control signals to the slave surgical device while a master-slave control relationship is provided between the master device and the slave surgical device.

Various implementations and examples of the master control device are described. In some implementations, the forces received on opposite sides of the elongated control body are caused by a pinching of the elongated control body between fingers of a user. In various implementations, the master device is mechanically ungrounded, or is coupled to a mechanically grounded linkage. In some implementations, a fluid is provided within a housing of the elongated control body, and the surface of the elongated control body includes deformable portions that are configured to deform from the forces received on opposite sides of the elongated control body, wherein the force sensor is configured to sense the deformation. In some implementations, the force sensor includes a pressure transducer configured to detect deformation of the deformable portions of the surface by detecting pressure of the fluid against the pressure transducer in response to the deformation. In some implementations, the force sensor includes one or more force-sensitive elements that are positioned to receive the forces applied to the surface of the elongated control body, the one or more force-sensitive elements resisting deformation from the forces received on the opposite sides of the elongated control body.

In some implementations, a method of operating a teleoperated system includes establishing a master-slave control relationship between a master device and a slave instrument, where the master device comprises an elongated control body including a surface. The method includes detecting a position and an orientation of the elongated control body in a working environment using at least one sensor, and providing first control signals to the slave instrument to move the slave instrument based on the first control signals, the first control signals based on the detected position and the detected orientation of the elongated control body. The method includes sensing amounts of forces received at the surface on opposite sides of the elongated control body resulting from engagement of fingers of a hand of a user and that provide a pinching of the surface of the control body between the fingers of the hand. The method includes providing second control signals to the slave instrument to control a function of the slave instrument based on the second control signals, the second control signals based on the sensed amounts of forces.

Various implementations and examples of the master control device are described. For example, in some implementations, the function of the slave instrument includes a function of an end effector of the slave instrument. In some implementations, sensing the amounts of forces includes sensing the amounts of the forces with respect to a force threshold, where force magnitude applied to the opposite sides of the elongated control body below the force threshold causes removal of the control of the function of the slave surgical instrument. In some implementations, the force threshold is a control force threshold, and the amounts of the forces are sensed with respect to a lock force threshold at a greater force magnitude than the control force threshold, where additional force magnitude applied to the sides of the elongated control body in excess of the lock threshold force level causes the function of the slave surgical instrument to be in a locked state. In some implementations, the amounts of the forces are sensed with respect to a release force threshold at a greater force magnitude than the control force threshold, where additional force magnitude applied to the sides of the elongated control body in excess of the release threshold force level causes a release of the locked state of the function of the slave surgical instrument.

In some implementations, sensing the amounts of the forces includes sensing a deformation of deformable portions of the surface of the elongated control body from the forces received on approximately opposite sides of the elongated control body, where a spine and rib structure is provided within the elongated control body, where the rib structure includes a plurality of ribs. The force threshold is based on a buckling force magnitude configured to cause a buckling of the plurality of ribs in response to the deformation of the deformable portions of the surface of the elongated control body. Additional force magnitude applied to the sides of the elongated control body in excess of the buckling force magnitude causes the control of the function of the slave instrument by the second control signals.

In some implementations, sensing the amounts of forces includes sensing a pressure of a fluid within a housing of the elongated control body by a pressure transducer, the fluid forced against the pressure transducer in response to the deformation of the deformable portions of the surface of the elongated control body. In some implementations, sensing the amounts of the forces is performed by a force sensor including one or more force-sensitive elements that are positioned to receive the forces applied to the surface of the elongated control body, the one or more force-sensitive elements opposing deformation by the forces received on opposite sides of the elongated control body. In some implementations, the elongated control body includes an input control coupled to the elongated control body, and the method further includes sensing activation of the input control by the hand of the user, and in response to sensing the activation, outputting an input control signal to the slave surgical instrument.

DETAILED DESCRIPTION

Figure 1:
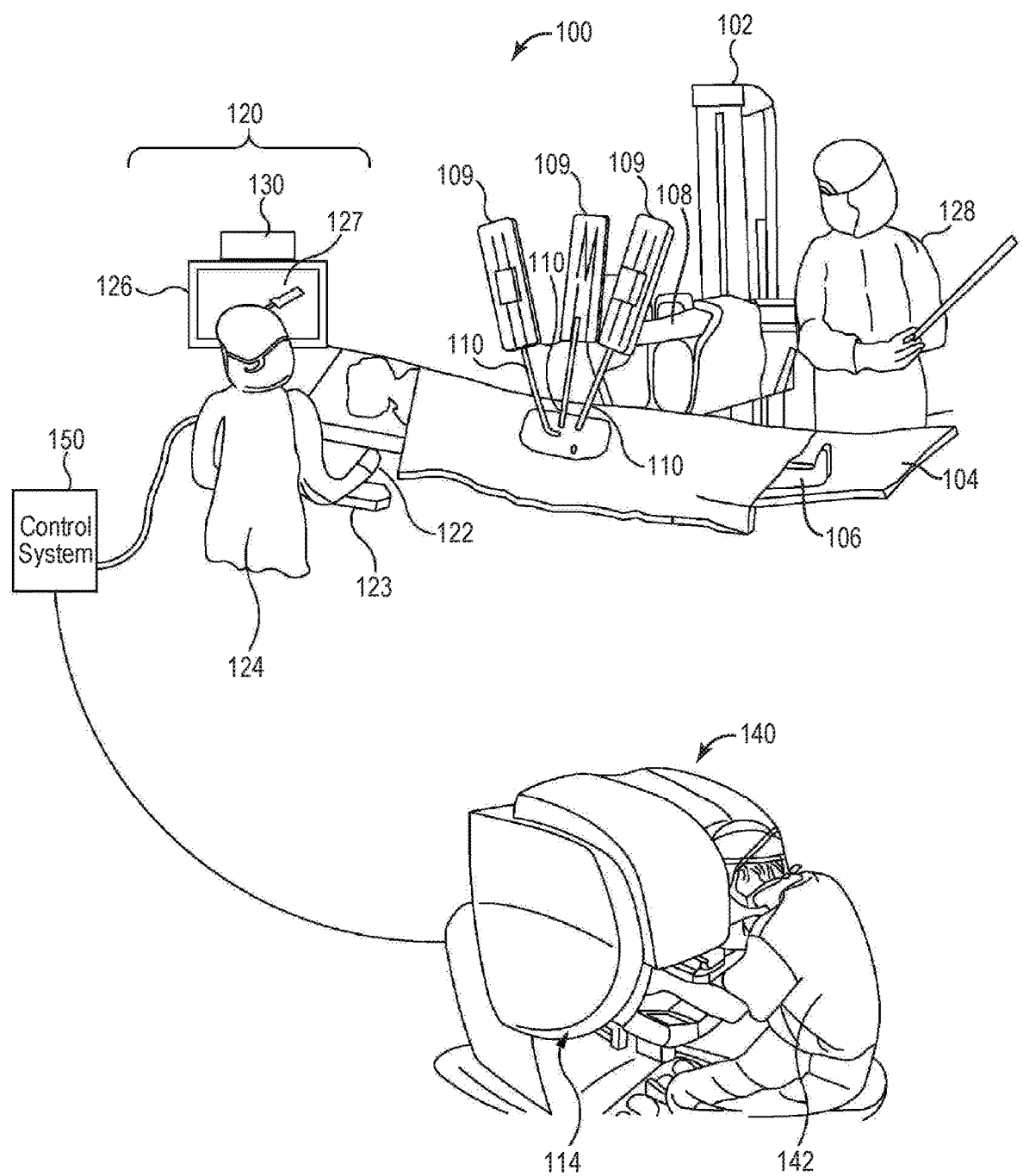
FIG. 1 is a diagrammatic view of an example teleoperated surgical system, according to some implementations.

Implementations relate to a master control device ("master controller"). As described in more detail herein, implementations provide a master controller enabling user control over multiple functions of a system, such as a teleoperated surgical system having a slave device. The master controller can be adapted to mechanically ungrounded operation by a user in a standing or sitting position, e.g., close to a patient or other site of operations. In some implementations, the master controller may be used in mechanically grounded operation. Functions activated by the master hand controller can include functions of instruments used in teleoperated systems, e.g., surgical tools and other instruments of the slave device used in treating patients, or other instruments in other types of procedures.

Described features of the master controller include a sensor system that detects a position and an orientation of the control body in a working environment as the master controller is held and moved by the hand of the user in the working environment. The controller includes a control body that is receptive to the forces or pressure provided by the fingers of the user that hold the control body, thus providing a grip control to control associated function(s) of the slave device. A force sensor of the controller senses the forces applied to the surface of the control body and provides sensor signals in accordance with the amounts of the forces received on approximately opposite sides of the control body caused by a finger grip of the user, e.g., pinching of the control body between the fingers of the user.

In some implementations, the surface of the control body includes deformable portions that deform from the forces received on the sides of the control body from the pinching grip of the user, and the force sensor senses the deformation. In some examples, a fluid (e.g., liquid or gas) is provided within a housing of the elongated control body, and the force sensor includes a pressure transducer that generates a sensor signal as a function of the pressure imposed by the fluid against the transducer in response to the deformation. For example, the walls of the control body can be made flexible and can deform by an amount in accordance with the amount of force of the holding fingers, causing an amount of fluid to be forced against the transducer based on the amount of deformation and finger force. To provide structure to the controller, a spine can be included, e.g., extending along a lengthwise axis of the control body. In further examples, a rib structure including ribs can be provided within the control body, e.g., around the spine. In some implementations, the ribs can have a buckling point, such that grip force applied to the control body past the occurrence of buckling commands a function of the slave device (e.g., grip control of an end effector). The rib buckling transition also creates a proprioceptive sensation of squeezing the instrument grip. In additional examples, the force sensor can be of other types, e.g., a strain gauge. In some implementations, the force sensor can include rigid surfaces that do not deform based on user pressure and can sense the forces applied by fingers to the sensor, e.g., a pressure-sensing film.

In various examples, the control body of the controller can be elongated, e.g., at least partially cylindrical, and axisymmetric about a lengthwise axis extending through the control body. In additional examples, the control body can be other shapes, e.g., spherical, partially spherical, an ellipsoid, etc. Input controls such as buttons, switches, etc. can be provided on the control body to output control signals in response to activations by fingers of the user.

The master controller features described herein provide various benefits. For example, ungrounded master controllers may be required to be operated by a user in various positions and orientations to control slave devices in corresponding movements. To provide accurate control, the controller should have few restrictions to its movement and manipulation by the fingers of the user (e.g., fingertip motion of the controller). However, many previous controllers provide constraints that restrict the manipulation of the controller in the user's hand. For example, finger bands or loops may be used to tie the user's fingers to grips of the controller. Such loops may restrict the user from manipulating the controller at the tips of the fingers where fine and precise motions of the controller can otherwise be made. Furthermore, some mechanically grounded master controllers may have similar issues with restriction of controller manipulation.

Implementations described herein can allow a master controller to be moved and oriented in space with reduced restrictions to movement while enabling the user to reliably and accurately control functions of a controlled slave device associated with a grip (e.g., squeezing or pinching) force on the controller. For example, the hand controller can be infinitely rotated about its central axis with a hand, e.g., the user's fingers are not constrained by finger loops or other constraints that fix the fingers to a position or surface of the hand controller. This can be particularly useful during a long-duration control task in what would be an awkward position if the controlling fingers were tied to a part of the hand controller. Furthermore, the controller allows more wrist range of motion than hand controllers that connect the controller to the hand (e.g., with finger loops). The orientation of the controller can be controlled extensively beyond the range of a user's wrist.

Furthermore, the described master controller provides a grip control that causes output of a grip control signal from the hand controller to activate a slave device function associated with gripping or pinching. The grip control is simple and easy for the user to initiate and actuate, e.g., based on deformation of a controller surface. Output of this grip control signal can be easy to maintain for reasonably long periods of time, e.g. by continually pinching the controller body in some implementations. Some implementations provide a threshold force level for the deformable surface which initiates grip control signaling by the controller, where the threshold force level is indicated haptically to the user via an internal structure of the master controller. The orientation of the hand controller is also well determined and controlled, e.g., without ambiguity, e.g., due to an elongated shape in some implementations.

Furthermore, the master controller allows the user to easily manipulate the wrist orientation of the hand controller without accidentally causing the grip control signal to be output. For example, described features of some implementations include an internal spine and/or ribs that can provide structure and support to a controller with an outer flexible or elastic housing structure, where the structure is stiff with normal handling until added force from pinching or squeezing causes it to become more compliant and deformable. This avoids a grip control that is too easy to squeeze by accident when the user is intending to adjust position and/or orientation of the controller. These features also impart a straight shape to such a flexible structure of the controller and avoid confusing and inaccurate flexing of the controller in different directions based on gravity, inertia, etc. as it is being moved.

Features described herein provide accurate and reliable manipulation of system functions using a master controller. Described features allow the controller to have large fingertip range of motion to provide accurate and precise control over slave instruments, without significantly restricting the range of controller motion. Features such as grip controls that are easy to actuate and are provided at any controller orientation can reduce fatigue in operating the hand controller to reduce inaccurate handling of the controller during controller operation, e.g. over long tasks. Described features are of high importance in procedures such as medical procedures in which controlled surgical instruments operate on a live patient, where accuracy and consistency in instrument control are required.

Various terms including "linear," "center," "parallel," "perpendicular," "aligned," or particular measurements or other units as used herein can be approximate, need not be exact, and can include typical engineering tolerances.

Some implementations herein may relate to various instruments and portions of instruments in terms of their state in three-dimensional space. As used herein, the term "position" refers to the location of an object or a portion of an object in a three dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw around the Cartesian X, Y, and Z axes). As used herein, the term "pose" refers to the position of an object or a portion of an object in at least one degree of translational freedom and to the orientation of that object or portion of the object in at least one degree of rotational freedom (up to six total degrees of freedom).

As used herein, a mechanically ungrounded master control device refers to a master controller that is unconstrained with respect to possible position and orientation motion in a large working environment (e.g., an operating area or room). Also, such a master controller is kinematically separated from the ground, e.g., not mechanically supported by a console, supports, or other object attached to the ground. In some implementations, a mechanically ungrounded master control device may be in tethered or untethered connection with one or more associated components such as control processors, data sources, sensors, power supplies, etc. For example, the master control device may be tethered, e.g., connected physically to these components via a cable or wire, or untethered, e.g., not physically connected to such components and in communication with the components via wireless communication signals.

Aspects of this invention augment the control capability of a computer-assisted teleoperated system through the use of one or more master controllers (e.g., one, two, three, or more) for providing instrument control in various procedures (surgical, procedures in extreme environments, or other procedures), instruction, supervision, proctoring, and other feedback to a user of the system. In some example implementations, master controllers may provide control of one or more of the operational surgical tools in the surgical environment or proxy surgical tools in a virtual environment. One example of a medical device system that may incorporate one or more of these master controllers (e.g., mechanically ungrounded or mechanically grounded) is the da Vinci® minimally invasive teleoperated medical system commercialized by Intuitive Surgical, Inc. of Sunnyvale, California.

FIG. 1 is a diagrammatic view of an example teleoperated surgical system 100, including one or more mechanically ungrounded master control devices, according to some implementations.

Figure 9:
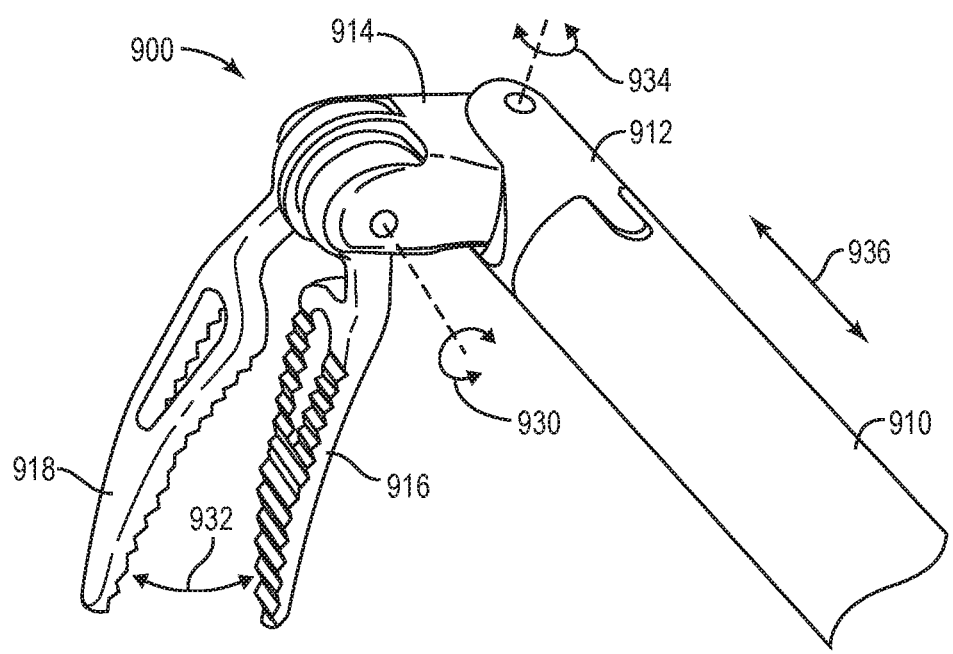
FIG. 9 is a perspective view of one example of an end effector which can be used with the slave device of FIGS. 1 and 12, according to some implementations.

As shown, the teleoperated surgical system 100 generally includes a teleoperated slave device 102 mounted to or near an operating table 104 (e.g., table, bed, or other support) on which a patient 106 is positioned. The example teleoperated slave device 102 includes a plurality of manipulator arms 108, each coupled to an instrument assembly 109. An instrument assembly 109 may include, for example, instruments 110 In some examples, instruments 110 may include surgical instruments or surgical tools. In some implementations, a surgical instrument can include a surgical end effector at its distal end, e.g., for treating tissue of the patient. In various implementations, surgical instruments can include cameras, e.g., cameras for use with surgical procedures. Some examples of an end effector for the teleoperated slave device 102 are shown in FIG. 9.

The teleoperated surgical system 100 includes an ungrounded master controller system 120. In this example, master controller system 120 includes one or more mechanically ungrounded master control input devices 122 ("ungrounded master controllers"), some implementations of which are described below, for use by a user 124. The master controller 122 includes at least one mechanically ungrounded, unpowered device contacted or grasped by hand of the user 124. In some implementations, two or more mechanically ungrounded unpowered devices can be used, e.g., each device grasped by a different hand of user 124. Example implementations of an ungrounded master controller 122 are described in more detail below. The master controller 122 can be operated in a sterile surgical field close to patient, as described below. An ergonomic support 123 (e.g., forearm rest) may be provided in the sterile surgical field to support the user's forearms or elbows as the user 124 manipulates master controller 122, e.g., during a surgical procedure.

In some implementations, the slave manipulator arms 108 and/or instrument systems 109 may be controlled to move and articulate the instruments 110 in response to manipulation of master controller 122 by the user 124, so that the user 124 can direct surgical procedures at internal surgical sites through minimally invasive surgical apertures. For example, one or more actuators coupled to the manipulator arms 108 and/or instrument systems 109 may output force to cause links or other portions of the arms 108 and/or instruments 110 to move in particular degrees of freedom in response to control signals received from the master controller 122.

The number of teleoperated surgical instruments 110 used at one time, and/or the number of arms 108 used in slave device 102, may depend on the medical procedure to be performed and the space constraints within the operating room, among other factors. If it is necessary to change one or more of the surgical instruments being used during a procedure, an assistant 128 may remove a surgical instrument no longer being used from its arm 108 or instrument assembly 109 and replace that surgical instrument with another surgical instrument from a tray in the operating room.

Some implementations of the teleoperated surgical system 100 can provide different modes of operation. In some examples, in a non-controlling mode (e.g., safe mode) of the teleoperated surgical system 100, the controlled motion of the teleoperated slave device 102 is disconnected from the master controller 122 in disconnected configuration, such that movement and other manipulation of the master controller 122 does not cause motion of the teleoperated slave device 102. In a controlling mode of the teleoperated system 100 (e.g., following mode), motion of the teleoperated slave device 102 can be controlled by the master controller 122 such that movement and other manipulation of the master controller 122 causes motion of the teleoperated slave device 102, e.g., during a surgical procedure. Some examples of such modes are described in greater detail below.

In this example, user 124 may be a surgeon controlling the movement of instrument systems 108 or a proctor providing supervision and/or instruction for a different surgeon or user (e.g., user or proctor surgeon 142). Each manipulator arm 108 and the teleoperated instrument assembly 109 controlled by that manipulator may be controllably coupled to and decoupled from mechanically ungrounded master controllers 122. For example, user 124 may sit or stand at the side of patient 106 while working in a sterile surgical field and view display device 126 during a surgical procedure. User 124 performs a medical procedure by manipulating at least master controller 122. In some examples, user 124 grasps master controller 122 in configurations described herein so that targeting and grasping involve intuitive pointing and pinching motions. As the user 124 moves master controller 122, sensed spatial information and sensed orientation information is provided to control system 110 based on the movement of master controller 122.

In some implementations, a hand-tracking transceiver 130 can be included in the ungrounded master controller system 120. For example, hand-tracking transceiver 130 can be positioned to generate a field, for example an electromagnetic field, an optical field (e.g., light beams), etc., in proximity to the user 124. The movement of master controller 122 in this field provides sensed spatial position and orientation information in a three-dimensional coordinate system, e.g., sensed by the transceiver 130 and/or other sensors (e.g., sensors positioned at other locations of the working volume). In some examples, the transceiver 130 can be or include an electromagnetic spatial tracking system, an inertial spatial tracking system, an optical spatial tracking system, a sonic spatial tracking system, etc. The device that senses and outputs sensed information may vary depending on the particular spatial tracking system or combination of tracking systems used. In each implementation, at least sensed position and orientation information for a master controller 122 are provided to a control system 150.

In some implementations, the ungrounded master controller system 120 also includes a display device 126. In some implementations, images captured by one or more cameras of the teleoperated slave device 102 (e.g., on an instrument assembly 109) can be transmitted to the display device 126 and/or transmitted to one or more other displays, e.g., a display coupled to the teleoperated slave device 102 (not shown), a display of the grounded input system 140, etc. For example, a surgical environment near or within the patient 106 and the real or virtual instruments controlled by the ungrounded master controller 122 can be displayed by the display device 126 and viewed by the user 124 while the user is operating the ungrounded master controller system 120. Display device 126 can provide a two dimensional image 127 and/or a three-dimensional image 127 of, for example, an end effector of a slave surgical instrument 110 and the surgical site. In some examples, display device 126 provides an output that the user perceives as a three-dimensional image that includes an image 127 of an end effector of a slave surgical instrument 110 and the surgical site. The end effector is located within a sterile surgical field. The three-dimensional image provides three-dimensional depth cues to permit user 124 to assess relative depths of instruments and patient anatomy. The three-dimensional depth cues permit user 124 to use visual feedback to steer the end effector of slave surgical instrument 110 using master controller 122 to precisely target and control features.

Various embodiments of an ungrounded master control device are disclosed in U.S. Pat. No. 8,521,331 B2 (issued on Aug. 27, 2013, titled "Patient-side Surgeon Interface For a Minimally Invasive, Teleoperated Surgical Instrument"), which is incorporated herein by reference in its entirety.

In some implementations, ungrounded master controller system 120 has at least one component within a sterile surgical field of the surgery. The sterile surgical field is a non-contaminant zone or space near the surgical site in which contaminants are reduced to reduce potential bacterial (or other) contamination to the surgical site during surgery. During surgery, the distal end of at least one teleoperated surgical instrument 110 is positioned within a sterile surgical field. In some implementations, the one or more components in the sterile field can include the master controller(s) 122. For example, master controller 122 is either sterile or draped so that master controller 122 may be safely positioned and used within a sterile surgical field for the surgery. This feature in combination with an image on display device 126 allows a user 124 to control teleoperated slave surgical instruments 110 from within the sterile surgical field. Thus, ungrounded master controller system 120 permits a user 124 to work within the sterile surgical field adjacent a patient 106 undergoing surgery.

Controlling minimally invasive slave surgical instruments 110 from within the sterile surgical field permits minimally invasive surgery combined with direct visualization of patient 106, teleoperated slave device 102, any manually operated surgical instruments, other machines and/or instruments being used in the surgery, etc., by user 124. In some examples, the proximity to patient 106 allows user 124 to control an end effector of teleoperated slave surgical instrument 110 together with one or more manually controlled instruments, such as a laparoscopic instrument or a stapler.

Ungrounded master controller system 120 can reduce operating room floor requirements for the teleoperated surgical system 100. Ungrounded master controller system 120 may provide a lower-cost alternative to a grounded input system 140 (e.g., surgeon console 141) in a conventional minimally invasive, teleoperated surgical system. For example, ungrounded master controller system 120 can improve safety by allowing user 124, who is performing the operation, to directly observe patient 106 and teleoperated slave device 102 while manipulating instruments 110. System 120 also allows the single user 124 to operate in the sterile surgical field and perform procedures which require coordinated use of manual surgical instruments and one or more teleoperated slave surgical instruments. System 120 promotes collaborative procedures without requiring additional large stand-alone surgeon consoles. In some implementations, assistant 128 may share system 120 to operate other surgical instruments. In addition, multiple users (e.g., surgeons or clinicians 124, 128, 142, etc.) may collaborate using a common display device 126.

In some implementations, the teleoperated surgical system 100 may also include a grounded input system 140, which allows a second user 142 (e.g., a surgeon, proctor surgeon, or other type of clinician) to view images of or representing the surgical site and to control the operation of the manipulator arms 108 and/or the instrument assemblies 109. In some implementations, the grounded input system 140 may be located at a console 141, e.g., a surgeon console, which can be located in the same room as operating table 104. In various implementations, the user 142 can be located in a different room or a completely different building from the patient 106. For example, the surgeon console 141 can be located outside the sterile surgical field.

In the example teleoperated system 100, grounded input system 140 includes one or more mechanically grounded master control input device(s) ("grounded master controllers") for controlling the manipulator arms 108 and the instrument assemblies 109. The grounded master controllers may include one or more of any number of a variety of coupled input devices, such as kinematically linked (mechanically grounded) hand grips, joysticks, trackballs, data gloves, trigger-guns, hand-operated controllers, voice recognition devices, touch screens, body motion or presence sensors, and the like. In some implementations, the grounded master controllers will be provided with the same degrees of freedom as the slave instruments of the teleoperated assembly to provide the operator with telepresence, the perception that the grounded master controllers are integral with the instruments so that the operator has a strong sense of directly controlling instruments as if present at the work site. In other implementations, the grounded master controllers may have more or fewer degrees of freedom than the associated slave instruments and still provide the operator with telepresence. In some implementations, the grounded master controllers are manual input devices which move in all six Cartesian degrees of freedom, and which may also include an actuatable handle for actuating instruments (for example, for closing grasping jaws, applying an electrical potential to an electrode, delivering a medicinal treatment, and the like). Such a grip function is an additional mechanical degree of freedom (i.e., a grip DOF). In some examples, each manipulator arm 108 and the teleoperated instrument system controlled by that manipulator arm may be controllably coupled to and decoupled from the grounded master controllers of input system 140. In some implementations, the grounded master controllers of the input system 140 include one or more features of the master controllers described in various implementations herein.

The teleoperated surgical system 100 also includes a control system 150. The control system 150 includes at least one memory and at least one processor (not shown), and typically a plurality of processors, for effecting control between the teleoperated slave device 102, the ungrounded master control system 120, and the grounded input system 140. The control system 150 also includes programmed instructions (e.g., a computer-readable medium storing the instructions) to implement some or all of the appropriate operations and blocks of methods in accordance with aspects disclosed herein.

For example, control system 150 maps sensed spatial motion data and sensed orientation data describing the master controller 122 in space to a common reference frame. Control system 150 may process the mapped data and generate commands to appropriately position an instrument 110, e.g., an end effector or tip, of teleoperated slave device 102 based on the movement (e.g., change of position and/or orientation) of master controller 122. Control system 150 can use a teleoperation servo control system to translate and to transfer the sensed motion of master controller 122 to an associated arm 108 of the teleoperated slave device 102 through control commands so that user 124 can manipulate the instruments 110 of the teleoperated slave device 102. Control system 150 can similarly generate commands based on activation or manipulation of input controls of the master controller 122 to perform other functions of the slave device 102 and or instruments 110, e.g., move jaws of an instrument end effector, activate a cutting tool or output energy, activate a suction or irrigation function, etc.

While control system 150 is shown as a single block in FIG. 1, the system may include two or more data processing circuits with one portion of the processing optionally being performed on or adjacent the teleoperated slave device 102, another portion of the processing being performed at the ungrounded master controller system 120, another portion of the processing being performed at the grounded input system 140, etc. Any of a wide variety of centralized or distributed data processing architectures may be employed. Similarly, the programmed instructions may be implemented as a number of separate programs or subroutines, or they may be integrated into a number of other aspects of the teleoperated systems described herein. In one embodiment, control system 150 supports one or more wireless communication protocols such as Bluetooth, IrDA, HomeRF, IEEE 802.11, DECT, and Wireless Telemetry.

In some implementations, user 124, from within the sterile surgical field, can control at least one proxy visual to a proctor surgeon 142 at the surgeon's console 141. For example, the proxy visual is visible both in display device 126 and in a display device viewed in surgeon console 141. Using master controller 122, user 124 can manipulate the proxy visual of a surgical instrument to demonstrate control and use of teleoperated slave surgical instruments 110 while second user (e.g., proctor surgeon) 142 uses master controllers of the surgeon console 141 to control a teleoperated slave instrument 110. Alternatively, second user 142 can control the proxy visual, using a master controller on the surgeon console 141, to instruct user 124. In some implementations, user 124 can telestrate (e.g., draw a freehand sketch over a moving or still video image), or can control a virtual hand or other pointer in the display. In some implementations, user 124 can demonstrate how to manipulate a master tool grip on the surgeon console 141 by manipulating a virtual image of master tool grip that is presented in the display devices 126 and on surgeon console 141. To facilitate proctoring, a proxy visual module (not shown) of the controller 150 can be processed as part of a vision processing subsystem. For example, the executing module receives position and orientation information, input control states (e.g., switch states, variable slider state, etc.), presence states, grip state, or other information from the controller device 122 and renders stereo images, which are composited with the endoscopic camera images in real time and displayed on any combination of surgeon console 141, display device 126, or any other display systems in the surgical environment.

In some implementations, a controlled teleoperated slave device 102 can be a virtual representation of a device, e.g., presented in a graphical training simulation provided by a computing device coupled to the teleoperated surgical system 100. For example, a user can manipulate master hand controller devices to control a displayed representation of an end effector in virtual space of the simulation, similarly as if the end effector were a physical object coupled to a physical slave device. Some implementations can use master controllers in training, e.g., demonstrate the use of instruments and controls of a workstation including controller devices.

In some implementations, non-teleoperated systems can also use one or more features of the master control devices as described herein. For example, various types of control systems and devices, peripherals, etc. can be used with described master controllers.

Some implementations can include one or more components of a teleoperated medical system such as a da Vinci® Surgical System (e.g., a Model IS3000 or IS4000, marketed as the da Vinci® Si® or da Vinci® Xi® Surgical System), commercialized by Intuitive Surgical, Inc. of Sunnyvale, California. Features disclosed herein may be implemented in various ways, including teleoperated and, if applicable, non-teleoperated (e.g., locally-controlled) implementations. Implementations on da Vinci® Surgical Systems are merely examples and are not to be considered as limiting the scope of the features disclosed herein. For example, different types of teleoperated systems having slave devices at worksites can make use of actuated controlled features described herein.

Figure 2:
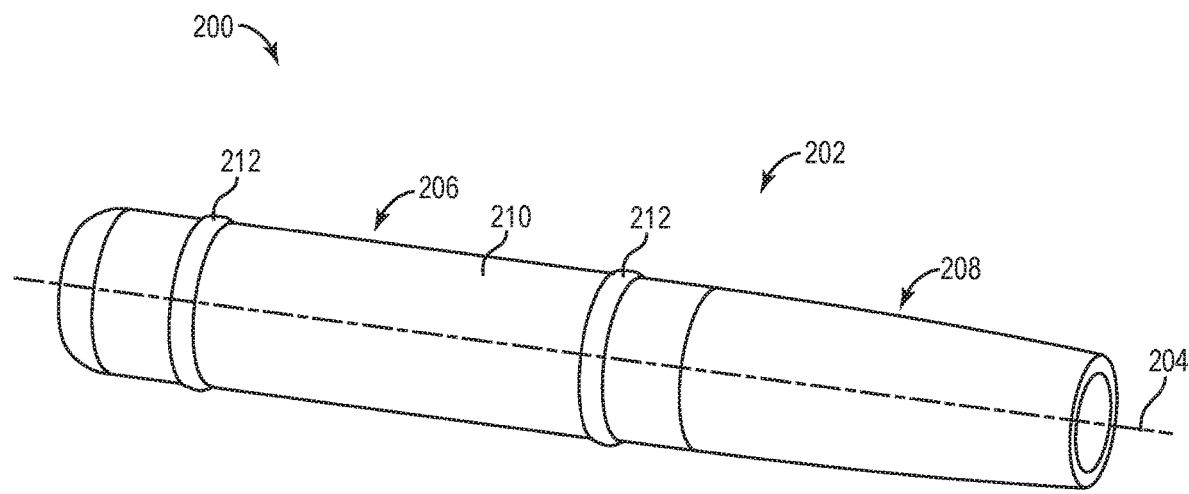
FIG. 2 is a perspective view of an example of a hand controller, according to some implementations.

FIG. 2 is a perspective view of an example of a hand controller 200, according to some implementations. In some examples, hand controller 200 can be an ungrounded master controller configured to be held by a user's hands and that is mechanically ungrounded during its operation. For example, hand controller 200 can be used as a master controller 122 as described with reference to FIG. 1. In further examples, hand controller 200 can be a grounded master controller configured to be held by a user's hands and that is mechanically grounded during its operation. For example, hand controller 200 can be used as a grounded master controller of the grounded input system 140 described with reference to FIG. 1. Hand controller 200 is contacted and held by a user to provide control signals to one or more systems in communication with the hand controller.

Hand controller 200 includes a control body 202. In this example, control body 202 is elongated such that its length is greater than its width and height. In some implementations, the control body 202 can be shaped approximately like a stylus. For example, the control body 202 can be approximately cylindrical or at least partially cylindrical as shown, or can be cigar-shaped, spindle-shaped (e.g., fusiform, such as cylindrical or elliptical cross-section and tapering at one end or at each end toward a central lengthwise axis 204), etc. Other shapes can be used in other implementations, e.g., any axisymmetric shape.

In this example, the control body 202 is axisymmetric about the central lengthwise axis 204 extending through the control body 202 and along which the control body 202 extends. In other implementations, the control body 202 can be asymmetric about the axis 204, e.g., have protrusions, extensions, or other features that extend out of one portion or area of the control body 202. The control body 202 can be moved in space and the position and/or orientation of the control body 202 (or another portion of the hand controller 200) in space can be sensed, some implementations of which are described below. Control body 202 can include a control grip portion 206 and an extension portion 208.

In still other implementations, the control body 202 can be other shapes, e.g., spherical or partially spherical (e.g., see FIG. 10), ellipsoid, super-ellipsoid, or rounded-square shapes; elongated with a square, rectangular, or other polygonal cross-section (with or without rounded corners); etc. For example, the control body 202 can be a continuously curving surface that encloses a volume.

Control grip portion 206 can be a portion of the control body 202 that is receptive to user input such as forces (e.g., pressure) provided by the user's fingers. For example, the control grip portion 206 can include a contiguous surface 210 that is configured to engage fingers of a hand of a user. In some implementations, the control grip portion 206 includes a force sensor (or multiple force sensors) configured to sense forces applied to one or more portions of the surface 210 by the user's fingers. In some examples, the forces from the user's fingers are simultaneously received on the surface 210, e.g., at portions of the surface 210 that are on approximately opposite sides of the control grip portion 206. For example, the user can provide a pinching grip that includes pinching the control body between two or more fingers of the user (e.g., a squeezing grip that includes squeezing of the control body between fingers of the user), where two pinching fingers provide the forces or pressure on sides ("opposing sides") of the control body, e.g., on portions of the surface 210 of the control grip portion 206 that are contact by pinching fingers and which are positioned on opposite sides of a central axis of the control body or on opposite sides of the pinched portion of the control body. The force sensor provides output of one or more control signals in accordance with the received forces.

In some implementations, the control grip portion 206 includes a surface 210 that is deformable (e.g., compressible) at one or more deformable portions, e.g., at any location of a surface 210 of the control grip portion 206 as described below, or at particular designated portions of the surface 210 in some implementations. For example, a portion of the surface 210 can deform in a direction approximately toward the central axis 204, e.g., in some implementations, create a shallow curve or depression in the surface in a direction approximately perpendicular to the surface toward the central axis 204. The deformation of the surface 210 can be caused by the forces simultaneously received on approximately opposite sides of the control body by fingers (e.g., forces provided by the pinching grip). This deformation allows the user's fingers to be moved toward each other (or one finger moving toward the other) as the deformable surface deforms at one or more locations. For example, this may feel to the user like squeezing a soft object. The surface allows such gripping fingers to be moved away from each other as the applied force is reduced and the deformed portions of the surface are restored to their neutral positions.

The deformation is sensed by the force sensor. In some implementations, the deformable surface is a surface of deformable walls of the housing of the control grip portion 206, where the walls are made of a flexible material that deforms at particular locations by an amount based on or in accordance with an amount of force provided by a grip force of the user's fingers at those particular locations. In some implementations, a fluid is provided within the housing of the control body 202, and the force sensor includes a pressure transducer. The deformation of the surface causes an amount of fluid to be forced against the transducer as pressure, where the pressure is based on the amount of deformation of (and force applied to) the portions of the surface 210. The pressure transducer detects the fluid pressure that is based on the amount of deformation of the deformable surface. Additional examples of deformable surface implementations are described below with respect to FIGS. 4 and 5.

In some implementations, other types of force sensors can be used to measure the force received on the control grip portion 206 based on deformation of surface 210 of the control grip portion 206 from the user's fingers, and/or based on displacement of a component of the force sensor. For example, force sensors such as strain gauges with elastic elements can be provided on the surface 210 or incorporated into the housing of the control grip portion 210. In additional examples, force sensors can be used such as electrical resistance strain gauges, foil strain gauges, semiconductor strain gauges, wire strain gauges, capacitive load cells, or other types of force sensors. Force sensors using linkages or flexures connected to displacement sensors such as hall effect sensors or linear variable differential transducers can be used. Such sensors can sense the distance that an element of the sensor travels as an indication of the amount of applied force.

In some implementations, one or more flexures or linkages can be used to provide force sensing surfaces on the controller 200. In one example, multiple individual flexible members can be oriented parallel to the central axis 204 and spaced around the central axis 204, e.g., at regular intervals to form an approximate cylinder. One side or both sides of the flexible members can be coupled to rigid end pieces of the control body 202 (e.g., extension portion 208). In some implementations, a flexible member flexes toward the central axis 204 in response to receiving force from the user's finger, and displacement sensor can sense the amount of displacement of the flexure (or an element connected to the flexure) to determine the amount of force applied by the user's finger. The flexed flexible member moves toward its neutral position, away from the central axis 204, when the force is reduced or removed from the flexible member, e.g., due to a restoring spring force of the flexure. In further examples, mechanical linkages can similarly be spaced about the central axis to allow one or more members of the linkages to move toward the central axis in response to force from a user's finger being applied to one of the members of the linkages.

In some implementations, the control grip portion 206 includes a force sensor that includes one or more force-sensitive elements that are positioned to receive forces applied by the fingers, e.g., the forces applied on approximately opposite sides of the control body by the fingers such as in the pinching grip described above. The force-sensitive elements can be rigid to oppose, resist, or substantially prevent their deformation by the grip forces applied by the user's fingers. For example, exerting pressure on force-sensitive elements positioned on opposite sides of the control body may feel to the user like squeezing a hard object. In some examples, the force sensor can include a pressure sensing film that is, e.g., wrapped around at least a portion of surface 210 of control grip portion 206, or multiple portions of such films positioned in locations on the control body 202, e.g., on opposing sides of the central axis 204. In another example, the force sensor can be a piezoelectric crystal force sensor that can sense a force applied by a finger to its force-sensitive element without substantial deformation or compression of the surface of that element. Strain gauges can be configured and used to sense the grip forces without user-noticeable deformation. For example, the strain gauge can be implemented as a component that is stiff and has less compliance compared to the structure or skin of the user's finger tips, thus rendering the sensation of a hard or stiff object to the user. Other types of sensors than can sense force without user-noticeable deformation of force-sensing elements can alternatively be used.

The sensing of force on the surface 210 provided by the user's finger causes the hand controller (e.g., the force sensor) to send signals describing the force to one or more control circuits of the system to which the controller 200 is connected, e.g., to control system 150 of teleoperated surgical system 100 or other system. For example, the magnitude or amount of force sensed resulting from the user's grip can be converted into electrical signals that are output by the force sensor. In some implementations, the sensed force can be a resultant force that results from both applied forces of a pinching grip of the user's fingers. In some implementations, the sensed force can be multiple individual forces, e.g., an individual force applied on one or more sides of the control grip portion 206 by a respective finger of the user's hand. In some examples, the control circuits provide control signals to the teleoperated slave device 102, an example of which is described with reference to FIG. 9. For example, the amounts of forces applied to the surface of the control grip portion 206 (e.g., in a pinching grip) can be used to control jaws or other components, or any of various degrees of freedom, of an end effector of a controlled slave device (e.g., teleoperated slave device 102). In some examples, the applied pinching force on the control grip portion 206 can correspondingly move forceps, pliers, or other instrument end effectors of the teleoperated slave device, or can activate another type of function of a controlled slave device (e.g., application of energy, suction, irrigation, etc.).

Hand controller 200 can be easily and infinitely rotated about its central axis with a hand, e.g., fingers are not constrained by finger loops or other constraints that fix the fingers to a position or surface of the hand controller. Hand controller 200 has more wrist range of motion than hand controllers that connect the controller to the hand (e.g., with finger loops). The orientation of the hand controller 200 can be controlled well beyond the range of one's wrist.

The ease of moving the hand controller 200 with respect to the operating hand can be advantageous in implementations providing detected gestures. For example, some implementations can detect different orientations, positions, and/or motions of the hand controller 200 in space as gestures that can be used to activate or command various functions in a teleoperated system (e.g., gesture poses and/or gesture trajectories). For example, a first gesture pose can be to align the control body 202 (e.g., based on the longitudinal axis 204) vertically in space pointing the distal end in one direction, which commands a first function of the system, and a second gesture pose can be to align the control body 202 vertically and pointing in the opposite direction, which commands a second function of the system.

In some implementations, multiple different grip positions can be designated on the control grip portion 206 to receive grip (e.g., pinching) forces and provide a control signal based on those forces. In some implementations, the particular grip portion that receives the grip forces can be determined. Each different available grip position can provide a different command or control signal. For example, a first grip position can be provided at distal portion of the control grip portion 206, and a second grip position can be provided at a proximate location of the control grip portion 206 that is closer to the proximate end of the controller 200 than the first grip position. In some examples, each grip position can be associated with its own force sensor, such that the associated sensor signal output by the force sensor indicates which grip position is being gripped by the fingers of the user. In some implementations providing a flexible housing for the control grip portion 206 and sensing a fluid with a single force transducer (as described for FIGS. 4 and 5), an additional sensor can be provided at each grip position to detect the presence of the user's fingers at the associated grip position and output an associated sensor signal. For example, a first sensor (e.g., optical sensor, capacitive sensor, etc.) can detect when the user's fingers are applied at the first grip position, and a second similar sensor can detect when the user's fingers are applied at the second grip position.

In some implementations, the control grip portion 206 can include one or more grips (not shown) which each provide a designated surface at which to contact one or more user's fingers. For example, two grips can be positioned at opposite sides of the control body 202. Each such grip can include a surface that is shaped to receive a fingertip or finger pad of the user. In various example implementations, a grip can have a contact surface that is flat (e.g., parallel to the axis 204), concave (curved inward to form a valley to fit a finger), or convex (curved outward to form a bump or shell engaged by the finger) to provide engagement and secure contact with fingers of the operating hand. The grips can have a tapered surface in some examples. Some implementations can provide protrusions that extend outwardly from the grip in which to cradle a finger on the sides of the finger, or an aperture in which a finger is inserted. Some implementations of a grip can include texturing such as bumps, ridges, or other patterns of features (some examples described below) on the surface of the grip to engage the user's finger with more friction and grip than a smoother surface. A multiple-finger grip can be used in some implementations, where multiple adjacent fingers engage a single grip. For example, a grip can include adjacent concave depressions to engage two or three fingers side-by-side, e.g., the second and third fingers, the third and fourth fingers, or the second, third, and fourth fingers (e.g., with the other grip 206 engaging the thumb).

In some implementations, one or more physical features such as bands 212 can be provided on the surface 210 of the control grip portion 206. Bands 212 can extend entirely around the circumference of the surface 210 (or around any portion of the control body 202), e.g., to allow the user's fingers to contact the bands 212 at any rotational position of the controller 200 about axis 204 in the user's hand. In some implementations, one or more bands 212 can extend partially around the circumference of the control body 202.

In some implementations, a band 212 can be positioned at a particular location on the control body 202 to be felt by the user's hand, and can guide the user's hand to grip the control body 202 at a desired position on the control grip portion 206.

In some implementations, a band 212 can designate a control point which can correspond to an origin of the degrees of freedom of a controlled slave device or instrument. The hand controller 200 can have a designated point which is a reference point for its motion, referred to herein as a control point, e.g., a master control point. The hand controller 200 can be considered to pivot about the master control point. A designated slave control point is also designated for a slave instrument currently controlled by the hand controller 200, where the slave control point is an origin for rotary degrees of freedom of the slave instrument, e.g., a point around which the slave instrument can pivot. The slave control point is designated to correspond to the master control point of the hand controller 200. In some implementations, when providing rotation, if the master control point is held stationary in space, the corresponding slave control point stays stationary in space, and other portions of the master controller and the salve instrument are correspondingly rotated or otherwise moved to accommodate the stationary control points.

In some implementations, one of the bands 212 is designated as the master control point and indicates the location of this control point in a tactile manner to the user. This allows the user to determine by feel the location of the location on the controller to which the control point of the slave instrument is mapped.

In various implementations, a control point can be defined using other physical features instead of or in addition to a band 212. For example, one or more bumps, divots, bulges can be provided. One or more portions of the surface 210 can be provided with multiple bumps or divots. One or more textured portions, regions, or areas can be provided to indicate a control point, which have a surface texture that is different than and contrasts in feel with a surface texture of surfaces surrounding the textured area. For example, a textured region can be provided with a rough surface like sandpaper, compared to smoother surfaces surrounding this area. Other physical features can also or alternatively be provided to indicate the control point of the hand controller 200 via the user's contact with the surface of the hand controller.

In some implementations, a control point can also or alternatively be marked or defined visually to, e.g., allow a user to visually find the control point and place his or her fingers with respect to the control point. For example, a contrasting stripe of color or shading can be provided on the surface of the controller to indicate the position of the control point.

In some implementations, one or more of the bands 212 or other physical features can be input controls, or portions thereof, that allow the user's hand to selectively output a control signal by activating the band input control. Input controls are further described below. For example, a band 212 can include an optical sensor, pressure sensor, button, switch, or other input control that can be activated by a finger of the user's hand. In one example, a band 212 can be a moving portion of a switch that slides parallel to the central axis 204 to open and close the switch. A bump, button, or other feature can alternatively be provided. In some implementations, the input control can sense user-input position of a contacted control object, and/or rotation or movement of such an object, e.g., using a switch, joystick, scroll-wheel, trackball, touchpad, etc., and provide control signals in accordance with the position, rotation, or movement. In some examples, a band 212 or other input control (e.g., grip, knob, ring, wheel, etc.) can rotate, and its position sensed.

In some implementations, an extension portion 208 can be included in the control body 202 of the hand controller 200. Extension portion 208 is coupled to the control grip portion 206 and extends away from the control grip portion 206, e.g., parallel to central axis 204. Extension portion 208 can form a proximal end of the control grip portion 206. In some implementations, extension portion 208 and control grip portion 206 form a unitary control body 202. In some implementations, extension portion 208 is a separate member that is coupled to a separate control grip portion 206. In some implementations, extension portion 208 is removable from the control grip portion 206 and, for example, can be replaced at the proximal end of the control body 202 by a differently-sized and/or differently-shaped extension member.

In some examples, extension portion 208 can be a similar shape to the control grip portion 206, e.g., cylindrical, cigar-shaped, etc. In additional examples, extension portion 208 can have other shapes. For example, extension portion 208 can include a wider portion at the proximal end to contact the palm of the user's hand, e.g., at least a portion of a spherical surface such as a hemispherical surface or a similarly-curved surface at the furthest proximal end of extension portion 208. In other examples, extension portion 208 can have rectangular or other polygonal faces, rounded corners, etc.

In this example implementation, extension portion 208 has an symmetric shape with respect to revolution about a longitudinal axis of the control body 202. In some implementations, extension portion 208 has an asymmetric shape revolved about the longitudinal axis 204 of the control body 202. For example, a portion such as a handle portion can extend from extension portion 208 asymmetrically to one side of and, e.g., approximately perpendicularly to the longitudinal axis 204. In some examples, during operation of the hand controller 200, the handle portion can be receptive to and/or grasped by one or more fingers of the user, e.g., the third, fourth and/or fifth fingers. Some implementations can provide a rigid extension portion 208 that is not deformable by the user's hand, and other implementations can provide a deformable or flexible extension portion 208 or a deformable or flexible covering to extension portion 208, e.g., made of rubber, foam rubber, neoprene sponge, or other deformable material. Such materials can be used in any of the implementations including a flexible housing as described herein.

In some implementations, extension portion 208 at the proximal end of the controller can set the center of gravity of the hand controller 200 further toward the proximal end of the control body 202. For example, this may adjust the center of gravity to allow more balanced usage, e.g., if weight is provided at the distal end of the hand controller 200.

In some implementations, extension portion 208 and control grip portion 206 are rotatable about the longitudinal axis 204 of the control body 202 with respect to each other. In some examples, a rotary coupling is provided between control grip portion 206 and extension portion 208. For example, in such implementations, the control grip portion 206 can be rotated about the axis 204 with respect to the extension portion 208, e.g., by the user's fingers, while the extension portion 208 is held grounded (e.g., stationary) contacting the palm or other portion of the user's hand. Similarly, extension portion 208 can be rotated about the axis 204 with respect to the control grip portion 206. In some implementations, the extension portion 208 can pivot in one or more additional axes with respect to the control grip portion 206, e.g., using a spherical joint or rotary joint or coupling provided between control grip portion 206 and extension portion 208. In some implementations, the rotary position of extension portion 208 about axis 204, and/or the rotation or pivoting motion of extension portion 208 about axis 204, can be sensed using one or more sensors, e.g., coupled to the control grip portion 206 and/or extension portion 208.

In some implementations, extension portion 208 can be expanded or collapsed in its length or size to allow adjustment in controller size and customization to a particular user's hand. For example, extension portion 208 can have an expandable surface to allow it to be increased in its cross-sectional diameter, or can be configured to extend/collapse in a particular direction or along a particular axis (e.g., parallel to axis 204). In some implementations, extension portion 208 can be detachable and can be removed (disconnected) from control grip portion 206, e.g., if only fingertip control of the controller 200 is to be used. In some implementations, a differently-sized extension portion 208 can be connected to the control grip portion 206 in place of the removed extension member.

In some implementations, extension portion 208 can be moved or extended linearly, e.g., can be translatable along the longitudinal axis 204 independently of the control grip portion 206. For example, extension portion 208 can be adjusted along the axis 204 to fit a particular-sized hand of the user, e.g., such that the surface 210 is contacted by the user's fingers while extension portion 208 rests against or is positioned near the user's palm or side of hand. In some implementations, a sensor can be provided in hand controller 220 to sense the position and/or linear motion of the extension portion 208 parallel to the axis 204 and relative to the control grip portion 206. For example, a linear sensor, mechanical switch, optical encoder, optical sensor, or other type of sensor can be used as the sensor.

Some implementations of the controller 200 can provide a control body 202 that includes the control grip portion 206 and not the extension portion 208. For example, such a shorter control body 202 can, in some implementations, allow a greater orientation range of motion of the controller 200 by allowing the proximal end of control body 202 to pass through the space between thumb and fingers, and/or to be positioned near or within the palm of the user's hand. In some implementations, the extension portion 208 can be made shorter and/or smaller (e.g., smaller than shown in FIG. 2) to allow more range of motion of the controller 200 in the hand of the user.

One or more sensors can detect, and/or can enable the detection of, the position and orientation of the hand controller 200 in the working environment. Since the hand controller 200 is mechanically ungrounded in this implementation, the control body 202 is effectively unconstrained for both position and orientation motions within the user's reachable workspace and a sensing workspace. Some examples of sensing systems able to sense the position and orientation of the control body 202 are described above. Such a sensor tracks position and/or orientation of the hand controller 200 in a workspace (working environment) relative to a fixed reference point. In some examples, a sensor Cartesian coordinate system (Xs, Ys, Zs) may be generally centered at the sensor. In some applications, the reference coordinate system may be a finger grip coordinate system, such that any movements measured in the sensor coordinate system may be transformed by an applied transformation from the sensor coordinate system to the finger grip coordinate system. In various implementations, the sensor may be a six degree of freedom (6 DOF) electromagnetic (EM) sensor, an optical tracking sensor, a fiber optic shape sensor, or another type of sensor.

In some implementations, such a sensor (or sensor component) can be positioned at various locations on or in the housing of the hand controller 200, e.g., on the control grip portion 206 or extension portion 208. In some implementations, the sensor may be a component of a sensor system, where additional components of the sensor system are positioned external to the hand controller 200 (e.g., hand-tracking transceiver 130 of FIG. 1). In some examples, the control body 202 can include a component that can be tracked by a sensing system that is located externally to the hand controller 200, e.g., one or more magnets, electromagnetic signal emitters, optical patterns, etc. In some implementations, the control body 202 can include a receiving component that receives signals emitted by an external system to assist in determining position and/or orientation of the control body 202 in space. In some implementations, the control body 202 can include one or more sensors operative to sense and/or assist an external sensor in detecting position and orientation of the control body 202. For example, motion sensors (accelerometers, gyroscopes, etc.) can be used within the control body 202 in some implementations.

In some implementations, the hand controller 200 does not include a sensor or sensor component for tracking its position and orientation in the workspace, and an external sensor system can perform such tracking (e.g., one or more cameras capturing video and/or motion occurring in the workspace, and a control system detecting and tracking the hand controller in the workspace by examining the captured video or recorded sensor data, etc.).

In some examples, the position, orientation, and/or motion of the hand controller 200 in three-dimensional space can be sensed to control operation of a teleoperated slave device. For example, position, orientation, and motion of the hand controller with respect to a reference position in three-dimensional space can be used to control a corresponding position, orientation, and motion of an arm assembly and/or instrument of a slave device in its available workspace and degrees of freedom. In further examples, the sensor may track movements, such as the movements of the hand controller 200 and/or user's wrist and forearm, to control a slave device, e.g., rotate and/or translate an instrument end effector.

Some implementations of the hand controller 300 can include a distal element coupled at the distal end of the control body 202, e.g., at the opposite end of control body 202 from extension portion 208. The distal element 236 can, in some implementations, include one or more sensors or sensor components used for tracking the position and/or orientation of the hand controller 200 in space, e.g., in a working environment such as a surgical environment. For example, receivers, transmitters, motion sensors, and/or other sensor components can be provided in the distal element. In some implementations, a distal end and/or proximal end of the hand controller 200 may include a weighted component, e.g., to provide a particular weighted balance to the hand controller 200 and/or to provide a center of gravity at a particular portion of the hand controller 200.

In some implementations, hand controller 200 can also include one or more input controls (also referred to as an "activation control," "activation control switch," or "activation control button"). An input control includes one or more sensors (e.g., mechanical switches, optical sensors, magnetic sensors, capacitive sensors, pressure sensors, etc.) that detects user input, e.g., the engagement or activation of a user's finger with the input control. Input controls can be used to detect activations of control signals by the user by, e.g., detecting a position of a finger or a threshold amount of contact with a finger of the user's hand. In some examples, an input control is a physical pushbutton or sliding switch that is operative to be activated by user input, e.g., engaged, slid, or pressed downward by at least a portion of a finger of the user that is operating the hand controller 200.

Various other types of input controls can be also or alternatively be used to enable user activation of a control signal, e.g., optical sensor areas, capacitive sensor areas, pressure sensors, wheels, knobs, etc. The activation of an input control causes a control signal to be output by the input control, e.g., to a control system. The control system can be in the housing of the hand controller 200 and/or in a separate device in communication with the hand controller (e.g., as described for control system 150 of FIG. 1). In some examples, the control signal can cause activation of a particular function provided by a system in communication with the input control as described above.

Input controls can be provided at any surface or portions of the hand controller, e.g., on the control grip portion 206, extension portion 208 (e.g., at the proximal end of the hand controller 200 or on a different portion of the surface of the extension portion 208), etc. In further examples, one or more types of input controls can be provided on a extended handle portion of the extension portion 208. In some implementations, the hand controller 200 can include one or more presence sensors that detect that a user's hand is engaged with and/or operating the hand controller 200. For example, optical sensors, pressure sensors, etc. can be used, e.g., at the surface 210, at grips on the surface 210, at the extension portion 208, at region 212, and/or at other areas of the controller 200. For example, the presence sensors can be used to determine whether a user is operating the hand controller, while the input control can be used to sense user input to cause activation of particular system functions.

In some examples of input controls, one or more finger switches can be provided on the control grip portion 206 to enable control of one or more functions of the teleoperated system. The finger switch can be a sliding switch (e.g., translatable parallel to the axis 204), or can be a press switch or button, optical sensor area, or other form of switch activatable by a finger. The finger switch can engage a user's finger during operation of the hand controller 200. For example, the finger switch can be engaged by a user's finger that is located between two other fingers that pinch the control grip portion 206. In some examples, a thumb contacts one side of the control grip portion 206, a third, fourth or fifth finger contacts the opposite side of the control grip portion 206, and a second (e.g., index) finger between the thumb and third finger operates the finger switch on the surface 210 of the control grip portion 206.

In additional examples, the input controls can include a ring switch provided, e.g., between the extension portion 208 and the control grip portion 206, on the control grip portion 206, or on the extension portion 208. In some examples, the switch can include a ring or other element, e.g., a ring similar to a band 212 with a larger cross-sectional diameter, that can be centered on the central axis 204 of the hand controller. The switch activates (e.g., closes or opens) if the ring is linearly translated by the user's hand with respect to extension portion 208 and control grip portion 206 along the central (longitudinal) axis 204. For example, pressing the ring to move in a direction toward the proximal end of the hand controller 200 can cause the switch to close, which causes a control signal to be sent to the control system to trigger an associated function of, e.g., the slave device or the teleoperated system 100 (e.g., camera mode activation, a clutch control to enter or exit controlling mode, etc.).

The ring switch can be provided in a position allowing easy access to the switch by a variety of fingers of the hand operating the controller 200. Since the ring of the switch extends fully around the controller (around axis 204), the switch is accessible to fingers on any side of the controller 200, around its cylindrical circumference, regardless of the particular orientation of the hand controller in space with respect to the user's fingers. For example, a third, fourth, or fifth finger (not used in squeezing the control grip portion 206) can move the ring of the switch toward the palm of the user (e.g., toward the proximal end of the hand controller 200). In some implementations, the ring can receive a restoring force provided by a spring or other actuator, which causes the ring to return to its (unactivated) position if the activating finger removes sufficient force that was applied on the ring.

In some implementations, a switch is located distal of the gripped location of the control grip portion 206. For example, a switch can be located at a location of the control grip portion 206 at or near the distal (left) band 212 as shown in FIG. 2. In some implementations, a switch located at the grip location, or proximal of the gripped location (e.g., on or closer to extension portion 208), then fingers or hand may be more likely to accidentally touch or activate the switch during handling of the controller for grip or orientation. In some examples, the distal switch can be a ring similar to the ring switch described above to allow uniform access by the fingers independent of roll position along the axis 204.

Other switches can be positioned at other portions of the hand controller 200. In some implementations, various types of controls can be provided on the hand controller to provide input signals based on physical manipulation of the controls by the user's hand, such as dials, knobs, wheels, dials, buttons, sliders, trackpads or capacitive sensors, joysticks, trackballs, pivoting switches, etc. In some examples, an input control can be a control wheel positioned on the control body 202, where the wheel can be rotated by a user's finger to provide a user-adjusted control signal based on the position or motion of the control wheel that can be used, e.g., to cause adjustment of parameters or functions of the teleoperated system 100, scroll displayed information on a display screen, etc. In some implementations, an input control can include a touch-sensing area positioned at one or more particular locations on the surface 210 of control grip portion 206 or on the extension portion 208, e.g., a touchpad, scroll area, touchscreen, etc. A variety of other types of controls can be positioned in these and other portions of the hand controller 200. In some examples, such types of controls can be located distal of a gripped location of the control body 202, or alternatively proximal of the gripped location.

In some examples, particular control functions of a teleoperated slave device can be mapped to the activation of input controls of the hand controller 200. Such functions can include, for example, a swap function allowing control of a first telemanipulator arm or instrument by the hand controller 200 to be swapped to a second arm or instrument; a camera function and/or clutch function; a user interface scroll function, allowing scrolling of displayed interface elements; energy output for slave instruments mapped to the input control, etc.

In some implementations, one or more physical connections, such as tethered connections, can be connected to and extend out of the control body 202, e.g., extend out of the control grip portion 206 and/or the extension portion 208. For example, the tethered connections can be cables that are attached to a control system, e.g., control system 150 of FIG. 1. In some implementations hand controller 200 is not tethered by physical connections, and can communicate with the control system via wireless signal communications. For example, a wireless transmitter can be provided in some implementations within the control body 202, where the transmitter is configured to send wireless signals to a master control system based on position, orientation, and/or motion of the control body 202 in space, based on the grip forces of fingers on the surface of the hand controller, and/or based on the activations of switches and other controls of the hand controller as described herein.

Figure 15:
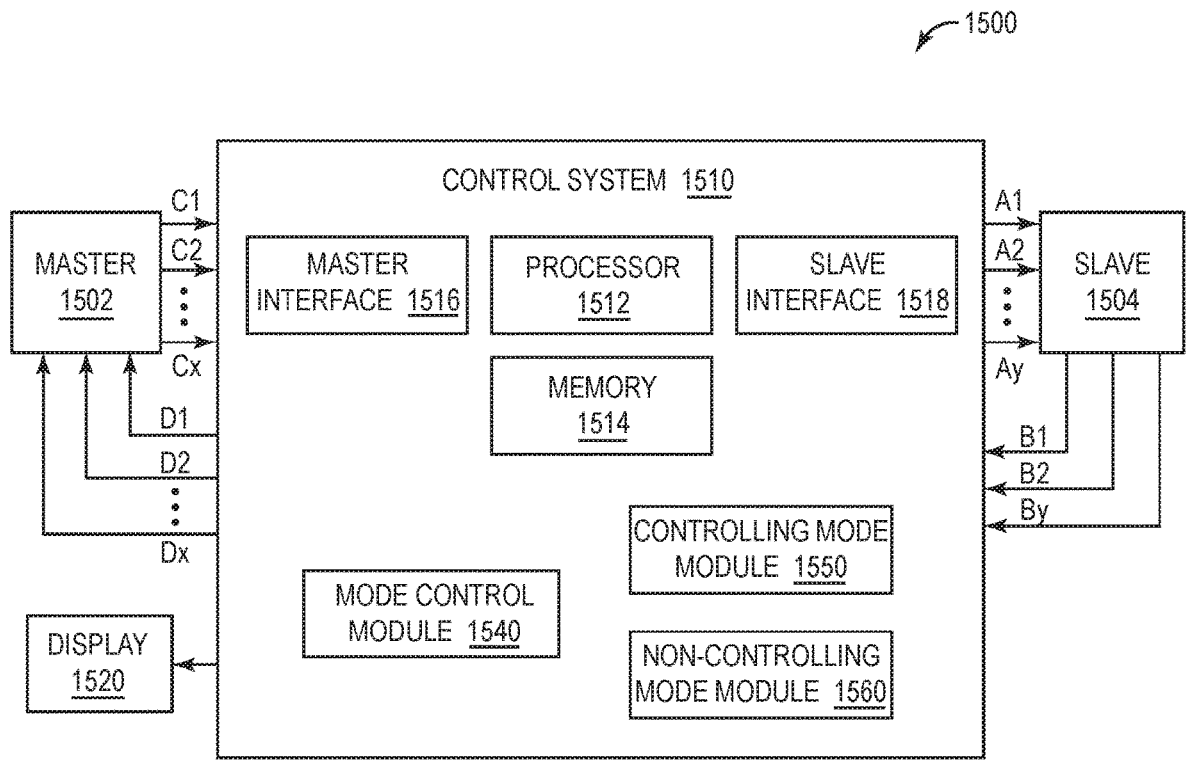
FIG. 15 is a block diagram of an example master-slave system, which can be used for one or more implementations described herein.

Various functions described herein may be implemented using a computing system such as control system 1510 of FIG. 15. In some implementations, a computing system may be attached in a suitable location on the hand controller 200 (e.g., in the control grip portion 206 or other location). In some implementations, the control system is implemented external to and communicates with the hand controller 200.

In some implementations, the hand controller 200 can be a mechanically grounded controller. For example, the control body 202 can be coupled to a mechanical linkage that is coupled to the ground or an object connected to ground, providing a stable platform for the use of the hand controller 200. For example, a grounded mechanical linkage can be connected to the control body 202, e.g., with one or more rotary couplings, ball joints, or other couplings, including linear joints. The mechanical linkage can provide six or more degrees of freedom to the hand controller. Some examples of such linkages and grounded hand controllers are described below with reference to FIGS. 11 and 12 and in U.S. Pat. No. 6,714,839 B2, which is incorporated herein by reference.

Figure 3:
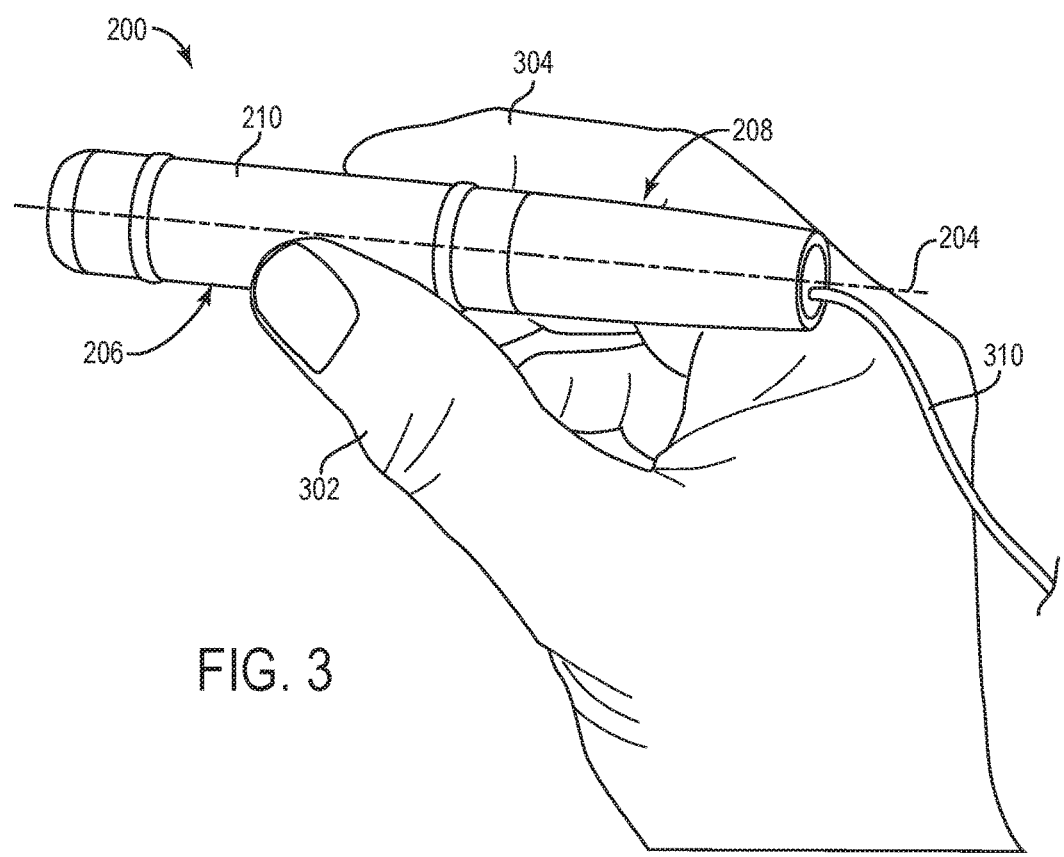
FIG. 3 is a perspective view of the hand controller of FIG. 2 being manipulated by a user's hand, according to some implementations.

FIG. 3 is a perspective view of the master hand controller 200 being manipulated by a user's hand, according to some implementations. In this example, the user's thumb 302 is engaged with a first portion of (e.g., location on) surface 210. The user's second finger 304 is engaged with a second, different portion of (e.g., location on) surface 210 that is approximately opposite to the first location, e.g., opposite via an axis extending from the first surface to the second surface through the control body 206 and approximately intersecting the central axis 204.

The user's fingers 302 and 304 may manipulate the position and orientation of the controller 200 in the working environment, e.g., using just the fingertip of these fingers to provide precise and accurate movement of the controller. The extension portion 208 is on the proximal end of the control body 202 and may contact the user's hand during some manipulations of the controller 200. For some manipulations, extension portion 208 may engage with the user's palm, e.g., contact the palm to allow a more reliable grip on the hand controller 200 by the user's hand while gripping and providing forces on the surface 210 with fingers 302 and 304.

The implementation shown in FIG. 3 includes an example of a tether connection (e.g., electrical wire or cable) 310 extending from the extension portion 208 at the proximal end of the hand controller 200. The connection 310 can be connected to a control system as described above and used to communicate electronic signals to and from the hand controller 200. In this example, the user can manipulate the hand controller 200 while the tethered connection 310 extends out on the side of the user's hand or over the top side of the user's hand. In some implementations, such a proximal end tether connection can provide increased security due to the weight of the tether being closer to the user's hand, and, compared to a distal end tether connection, may allow fewer collisions with the tether since the tether is closer to the user and further within the workspace controlled by the user. In some implementations, a tethered connection can be connected and extended from the distal end of the hand controller 200, as described above.

Figure 4:
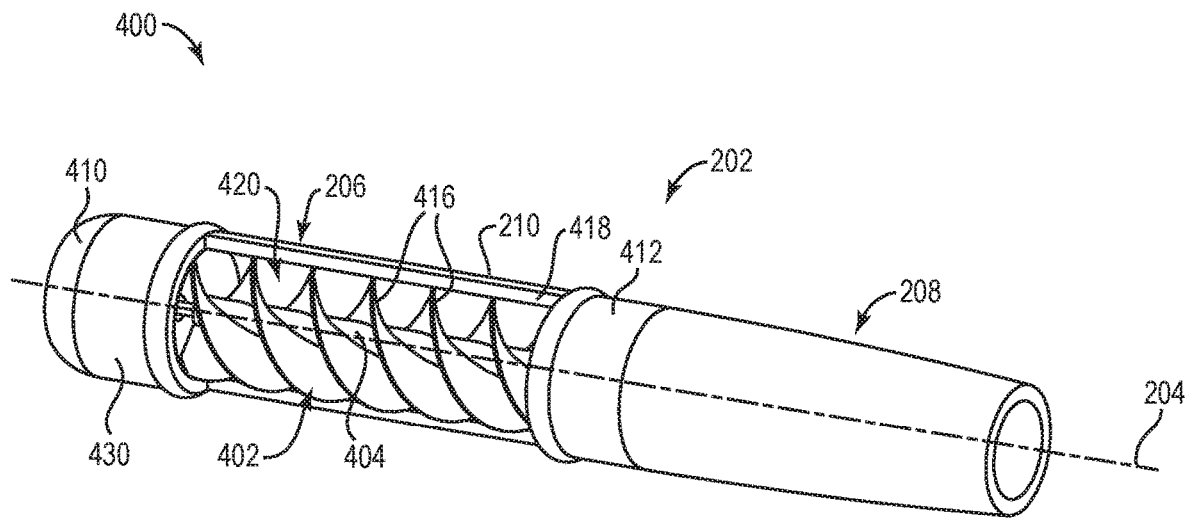
FIG. 4 is a perspective view of an example hand controller showing an example interior structure, according to some implementations.
Figure 5:
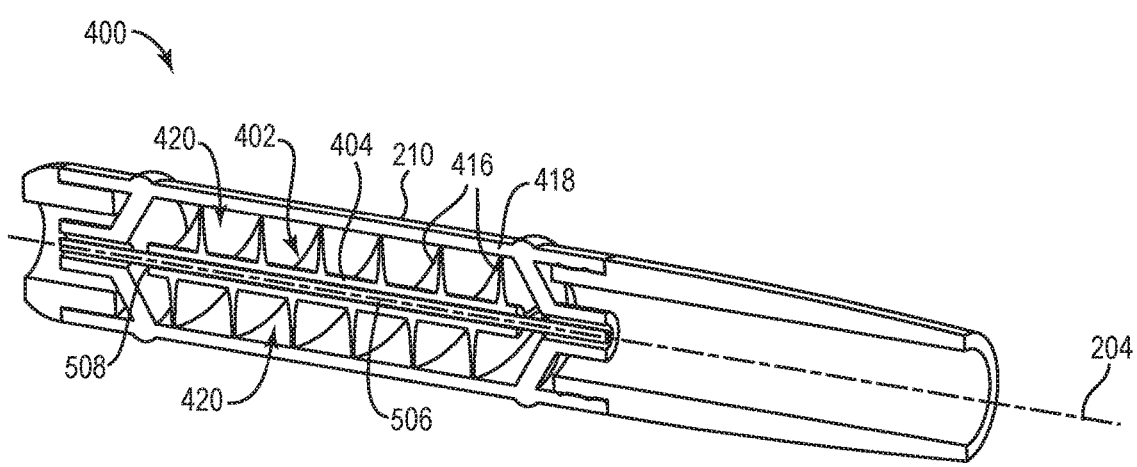
FIG. 5 is a perspective view of the hand controller of FIG. 4 in which the interior of the hand controller is shown in a cross-sectional view, according to some implementations.

FIG. 4 is a perspective view of an example master hand controller 400 showing an example interior structure, according to some implementations. FIG. 5 is a perspective view of hand controller 400 in which the interior of the hand controller 400 is shown in a cross-sectional view. Hand controller 400 is an example implementation for hand controller 200 of FIG. 2, and elements of the hand controller 400 that are similar to hand controller 200 are numbered the same as in FIG. 2.

Surface 210 is a surface of an outer wall 418 of control body 206 that is cut away in FIG. 4 to reveal an interior of the control grip portion 206. Outer wall 418 forms a part of the housing of the control body 202 (other portions of the housing can include extension portion 208, end portions of the control body 202, etc.). In this example, outer wall 418 is flexible and soft, allowing its surface 210 to deform in response to applied pressure, e.g., from the user's fingers, similarly as described for some implementations of FIG. 2. Some examples of materials used for the wall 418 of the control grip portion 206 include thermoplastic elastomers such as thermoplastic polyurethane, curable elastomers such as silicone rubber, and 3D-printable elastomers. The deformable surface 210 provides physical displacement approximately proportional to the force the user's fingers are exerting on the control grip portion 206, unlike a rigid surface, thereby indicating to the user the amount of force exerted on the surface 210.

Hand controller 400 includes a spine structure 402 extending through the interior of the control grip portion 206 to provide stiffness and rigidity to the control grip portion 206 of the hand controller 400. In some examples, spine structure 402 is made of a semi-rigid material that is more rigid than the material of the structure (e.g., wall 418) of the deformable surfaces of the control grip portion 206. For example, the spine structure 402 can be made of a semi-flexible material such as polyurethane or other elastomer, etc. In some implementations, spine structure 402 can be centered on the central axis 204 of the control body 202. In some implementations, spine structure 402 can include a central shaft 404 centered on the central axis 204 which, for example, can connect the spine structure 402 to the housing of the control body 202, e.g., at the ends of the control grip portion 206. In some implementations, the central shaft 404 has a hollow central bore 506 (see FIG. 5) through which a rigid or stiff spine shaft 508 (shown in dashed lines) can extend. The spine shaft 508 adds additional stiffness to the spine structure 402. In some implementations, the spine shaft 508 can be made of a material that is stiffer and more rigid than the material of the central shaft 404 and ribs 416, e.g., a metal with increased stiffness and strength such as steel or stainless steel. In some implementations, spine structure 402 can be coupled between end portion 410 at the distal end of the control grip portion 206 and element 412 provided between the control grip portion 206 and the extension portion 208. For example, the shaft 508 extending through central bore 406 can be coupled to the end portion 410 and element 412. In some examples, end portion 410 and element 412 can be closed or sealed to contain a fluid inside the control grip portion, in implementations using such a fluid.

Spine structure 402 can include a rib structure, e.g., ribs 416, provide additional structural support to the walls of the control grip portion 206. In the example of FIGS. 4 and 5, spine structure 402 includes helical or spiral ribs 416, where ribs 416 are coupled to the central shaft 404 at an inner location and have an outer edge that contacts or near-contacts the inner surface of the wall 418 of the control grip portion 206.

In some examples, ribs 416 are part of a single protrusion that winds around the spine shaft 508 in a helical or spiral form, e.g., a continuous helix centered around the spine shaft. In various implementations, the ribs can be spokes, or portions of a helix, e.g., instead of a continuous helix. In other implementations, other shapes of ribs can be used. For example, a plurality of discs, wheels, rings, or spokes can be provided instead of helical or spiral ribs, and which have outer edges that contact or near-contact the inner surface of wall 418. In some implementations, near contact of the ribs to the wall 418 can allow tolerances for manufacturability, where the inside components of the control grip portion 206 can be molded and then inserted with, for example, a slip fit or interference fit into the wall 418. In various other implementations, the ribs can be individual spokes extending from central axis to outer wall and disconnected from each other, or can be disconnected portions of a helix, instead of a continuous helix of material.

In the example of FIGS. 4 and 5, an interior chamber 420 of the control grip portion 206 includes a fluid that fills the interior chamber 420 and that allows the surface 210 of the control grip portion 206 to deform and compress in response to applied force from the user's fingers. The fluid can be a non-compressible (or approximately non-compressible) liquid. In some implementations, the fluid can be a compressible fluid, e.g., a gas such as air. An advantage to using a gas such as air is that if the control grip portion 206 develops a leak, the gas flows out into the outside air instead of dripping or otherwise flowing out of the leak as a liquid.

In this example, the force sensor for sensing the force of the user's fingers on the surface 210 of the control grip portion 206 can be a pressure transducer (e.g., one or more pressure transducers) provided in or connected to the interior chamber 420 of the control grip portion 206. The transducer can sense a pressure of the fluid that is forced against the transducer in response to deformation of the surface 210 by one or more fingers of the user. In some implementations, the pressure transducer can be located at a location that allows for communication of fluid pressure to the transducer. For example, a pressure transducer can be located at either end of the interior chamber 420. In some examples, a pressure transducer can be located within or near part 430, or alternatively can be positioned at a different location at the distal end of the control body 202 within the interior of the control grip portion 206. In some implementations, the pressure transducer can be positioned at other locations in the interior chamber 420, e.g., at or near the element 412, in a central area between portion 410 and element 412, etc. The pressure transducer (referred to generally as 430) generates a sensor signal that is a function of the pressure imposed by the fluid on the transducer. Thus, the wall 418 of the control grip portion 206 deforms by an amount in accordance with the amount of force of the gripping fingers, and this deformation causes an amount of fluid to be forced against the pressure transducer, where the amount of fluid is based on the amount of surface deformation (and thus amount of applied force from the user's grip fingers).

In some implementations, the pressure transducer can be located at a different location of the hand controller 400, e.g., where the fluid can be guided to that location, e.g., via one or more ducts or other channels in the control body 202. For example, the fluid can be guided to contact a pressure transducer positioned at the extension portion 208 (e.g., at the proximal tip of the extension portion 208) or other location at the proximal end or distal end of the hand controller 400.

In some implementations, a control device or system receives the sensor signal from the pressure transducer and checks whether the sensor signals indicates a threshold amount of pressure has been detected, where the threshold pressure indicates that a grip control signal has been commanded by the user. The amount of detected pressure over the threshold pressure can indicate the amount of deformation of the surface 210 of the control grip portion 206, and thus indicate the amount of force of the user's grip and/or indicate a position of the fingers within a grip degree of freedom to control a function of the slave device.

When the user's fingers remove a sufficient amount of force from the surface 210, the deformable surface 210 returns to a neutral state. For example, with the pressure removed, the fluid equalizes in the interior chamber 420 and allows the surface 210 to move to the neutral state in which the depressed and deformed portion of the wall 418 is moved away from the central axis 204.

In other implementations, no spine structure 402 or other internal structure is provided in the control body 202, and the control grip portion 206 is supported by its wall 418. In some implementations in which the surface 210 is flexible, this may allow the hand controller 400 to flex more freely in the user's hand during operation.

The spine shaft 508 can provide rigidity and stiffness to the hand controller 400. For example, the shaft can maintain the hand controller 400 in a straight shape during manipulation of the hand controller 400, despite the outer wall 418 of the control grip portion 206 being flexible. The helical or spiral ribs 416 can provide additional support to the flexible wall 418 to maintain the controller 400 in a straight configuration, while still allowing the surface 210 of wall 418 to be deformed by finger pressure and to allow fluid in the interior to be compressed, forced, and sensed by the transducer. For example, in some implementations, the rib structure is made of a material that is more rigid than the structure of the housing of the hand controller 400, e.g., more rigid than the grippable wall 418.

In some implementations, the stiffness provided by the spine shaft prevents a user-intended or commanded orientation of the control body 202 in space from being unintentionally changed or bent by a gripping action of the user on the control body. Furthermore, the ribs can prevent or reduce manipulation forces received on the control grip portion 206 by the user's fingers from pressurizing the fluid in the interior of the control grip portion 206 to a threshold amount of pressure that indicates a command of a grip control signal. This allows the controller 400 to be gripped and manipulated by the user with reduced concern of inadvertent output of grip control signals by the controller 400.

Spine structure 402 and/or ribs 416 can be made of a semi-flexible material that allows the spine structure 402 to flex with the compression of surface 210 and/or with bending of the control body 202. The spine structure 402, however, provides an amount of stiffness to the control grip portion 206 that allows the hand controller 400 to retain its shape and provide a stable structure for manipulation by the user's hand. For example, the hand controller 400 that includes the spine structure 402 with the ribs 416 starts to flex or buckle based on a threshold amount of force applied to the surface of the control grip portion 206. This threshold force provides a boundary between a regular operating grasp of the hand controller 400 for moving the controller 400 in the working environment, and a grip command grasp (pinch or squeeze) that provides an amount of force to command a grip control signal. This provides the user with a readily-perceived distinction between holding the controller and squeezing it to provide a grip control signal. Some example implementations are described with respect to FIGS. 6 and 7.

The force sensor, deformable surface, and liquid can be selected and positioned such that hysteresis between a user squeezing the surface and the output of a corresponding control grip signal is low. In addition, the deformation of the surface can be made to smoothly deform from user-applied force and smoothly return to a neutral position when sufficient amount of the user applied force is removed, such that manipulation of corresponding slave device is also smooth.

The hand controller 400 can allow the user to easily manipulate the wrist orientation of the hand controller without accidentally pinching or squeezing the surface 210 enough to cause a grip control signal to be output. Furthermore, output of the grip control signal from the hand controller 400 is simple for the user to initiate based on deformation of the surface 410 at any grip position in the user's hands. Output of this control signal is easy to maintain for reasonably long periods of time, e.g., by continually pinching the surface 210. The orientation of the hand controller is also well determined and controlled, e.g., without ambiguity.

A hand controller having a housing (e.g., outer wall 418) made of soft tubing without a spinal structure may have disadvantages in some implementations. For example, a problem with flexible housing (e.g., soft tubing) without an internal structure is that it may be "floppy" in the user's hand, e.g., may flex easily in different directions based on gravity, inertia, etc. as it is being moved. For example, instead of holding a shape extending in a straight line with an easily-implied orientation, such a hand controller can become bent into a curved shape, which can make the orientation confusing, and also cause roll motion to be coupled with unintended pitch and yaw motion. In contrast, an internal spine structure 402 as disclosed herein includes a central axial spine that imparts a straight shape to the outer flexible elastic structure of the hand controller.

In another example, soft tubing may be too easy to squeeze significantly by accident when the user is intending to adjust orientation. The ribs of the internal spine structure 402 disclosed herein can provide a structure that is stiff at first, until added force from squeezing causes it to become more compliant and deformable. For example, the helical rib of the spine structure can be stiff until it buckles.

Figure 6:
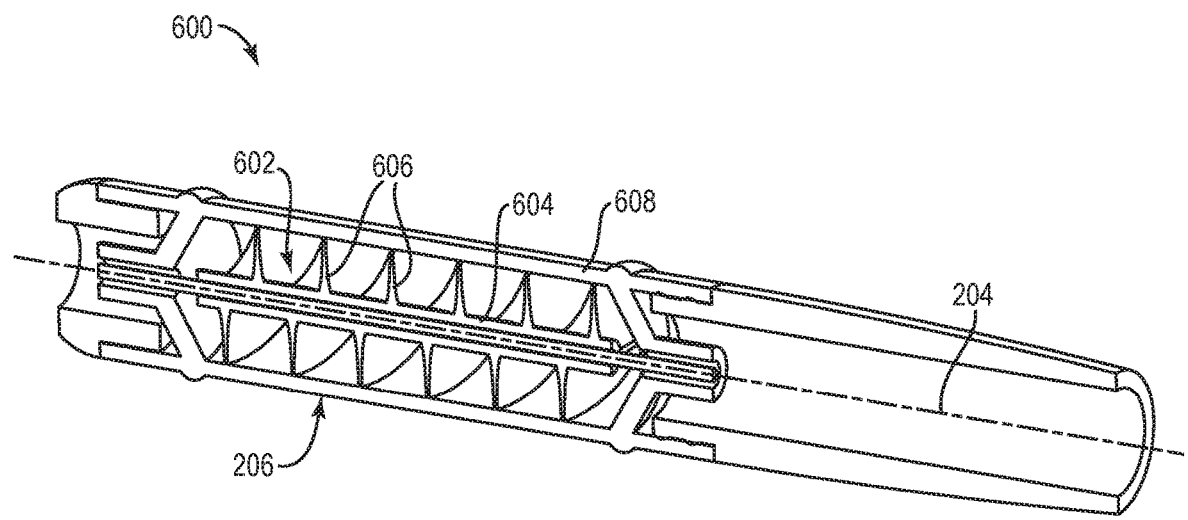
FIG. 6 is a perspective cross-sectional view of an example hand controller in which straight ribs are used in an interior rib structure, according to some implementations.

FIG. 6 is a perspective view of one implementation 600 of a hand controller according to features described herein. In FIG. 6, the interior of the hand controller 600 is shown as a radial cross section, cut through the central axis 204 of the hand controller 600.

A spine structure 602 includes a spine shaft 604 and ribs 606 that are coupled to the spine shaft 604, similarly to the spine structure 402 of FIGS. 4 and 5. In the example hand controller 600, ribs 606 are part of a single protrusion that winds around the spine shaft in a helical or spiral form, e.g., a continuous helix centered around the spine shaft similarly as in FIGS. 4 and 5. In various implementations, the ribs can be spokes, or portions of a helix, e.g., instead of a continuous helix. Ribs 606 and have an outer edge that contacts or near-contacts the inner surface of an outer wall 608 of the control grip portion 206. In some implementations, the interior of the control grip portion 206 of the hand controller 600 can include a fluid and transducer, similarly as described above.

In the example hand controller 600, ribs 606 are straight ribs that extend linearly from the central axis 204 and spine shaft 604 to the outer wall 608 as viewed in the radial cross section shown in FIG. 6. For example, the cross-section of straight ribs 606 shows that the straight ribs 606 do not have a bend in their length from the central axis 204 (spine shaft 604) to the outer wall 608.

This straight rib configuration can provide resistance to deformation of the outer wall from pressure or force from the users fingers. When subject to additional force, a straight rib will buckle, changing the spring rate of the compression action and creating a proprioceptive sensation to the user of squeezing a controller grip as the flexible walls deform inwardly toward the central axis 204. However, the magnitude of the threshold force required to cause the straight rib to buckle may not be predictable or consistent, and the direction of buckling of the straight rib may not be predictable, e.g., to the left or to the right of the rib in the view of FIG. 6, based on the characteristics of the force applied to each rib and the detailed particular physical structure of each rib. In some cases, the straight rib structure may require high magnitude force and/or unpredictable magnitude of force from the user before buckling, which can cause overshoot in grip position (e.g., in the amount of controller wall deformation toward the central axis 204) as the ribs suddenly buckle and become less stiff due to having buckled.

Figure 7:
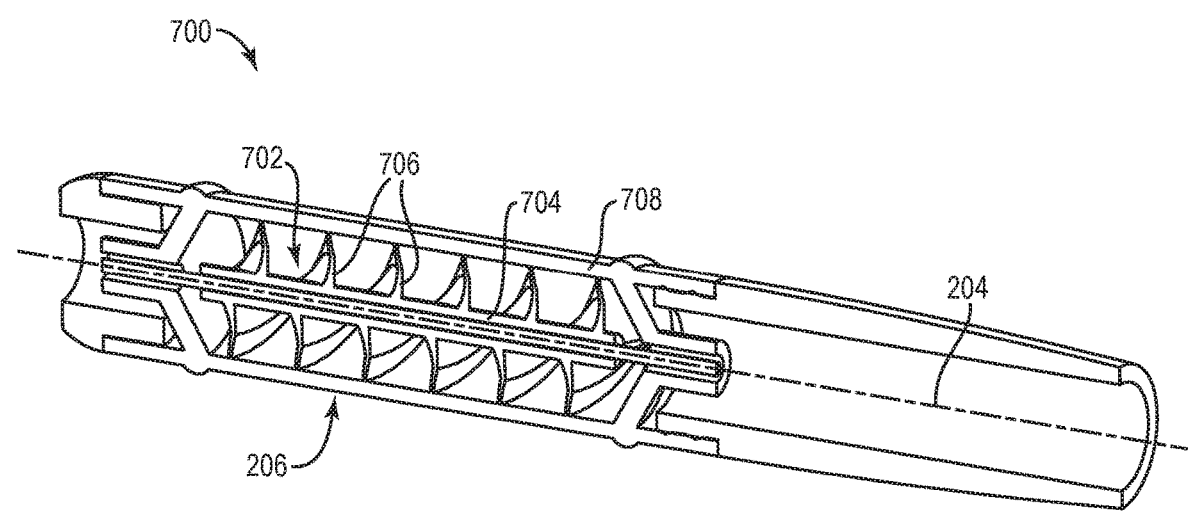
FIG. 7 is a perspective cross-sectional view of another example hand controller in which bent ribs are used in an interior rib structure, according to some implementations.

FIG. 7 is a perspective view of another implementation 700 of a hand controller according to features described herein. In FIG. 7, the interior of the hand controller 700 is shown as a radial cross section, cut through the central axis 204 of the hand controller 700.

A spine structure 702 includes a spine shaft 704 and ribs 706 that are coupled to the spine shaft 704, similarly to the spine structure 402 of FIGS. 4 and 5. In the example hand controller 700, ribs 706 are part of a single protrusion that winds around the spine shaft in a helical or spiral form, e.g., a continuous helix centered around the spine shaft similarly as in FIGS. 4 and 5. In various implementations, the ribs can be spokes, or portions of a helix, e.g., instead of a continuous helix. Ribs 706 and have an outer edge that contacts or near-contacts the inner surface of an outer wall 708 of the control grip portion 206. In some implementations, the interior of the control grip portion 206 of the hand controller 700 can include a fluid and transducer, similarly as described above.

In the example hand controller 700, ribs 706 are bent ribs that extend non-linearly from the central axis 204 and spine shaft 704 to the outer wall 708 as viewed in the radial cross section shown in FIG. 7. For example, the cross-section of bent ribs 706 shows that the bent ribs 706 have a bend (e.g., curve, bend, or angle) in their cross-sectional length from the central axis 204 (spine shaft 704) to the outer wall 708. In various implementations, the bend can be gradual like a curve, or can include one or more sharper changes in direction, e.g., each bend forming an angle between two straight portions of the rib.

This bent rib configuration can provide resistance to deformation of the outer wall from pressure or force from the users finger. When subject to additional force in excess of a threshold amount of force, a bent rib will buckle, removing some resistance to the user's force and creating a proprioceptive sensation to the user of squeezing a controller grip as the flexible walls deform inwardly toward the central axis 204. Using bent ribs 706, the buckling occurs in a known direction based on the direction of the bend in the rib. For example, a bent rib 706 having a bend toward the left will tend to buckle toward the left of the rib in the view of FIG. 7, since the bend orients the top of the rib to the left of the bottom of the rib that is coupled to the spine shaft 704. Furthermore, the bend allows a consistently smooth-feeling deformation of the controller's wall 608 to the user's hand when the threshold force has been exceeded.

In some implementations, the bend in the ribs biases the buckling to occur in one direction, and makes the threshold force that causes the buckling to be more predictable in comparison to buckling that occur with the straight ribs of FIG. 6. The bent ribs 706 can be designed such that a more predictable amount of force is required to cause the buckling, and a more predictable direction of buckling occurs by the ribs, compared to straight ribs. The bent configuration of ribs can create a smooth deformation in the wall from user grip force once the threshold force has been exceeded, in some implementations. Furthermore, the bent rib structure can reduce the occurrences of overshoot in grip position that may occur with straight ribs requiring high magnitude forces and/or unpredictable magnitude of forces to buckle as described with reference to FIG. 6.

In some implementations, the threshold force that causes the ribs to buckle can be used to distinguish and provide different control modes or states for the controller 700. For example, grip forces from the user on the wall 708 that are below the threshold force may be sensed by the transducer (or other sensor) but can be ignored with respect to the command of control signals. This range of grip force can be used by the user to grasp the controller 700, to move the controller in space, and to change the controller orientation in space. After the user feels one or more ribs 706 buckling when the grip force is at the threshold force, grip force magnitudes above that threshold force can be used to provide command signals from the controller. For example, the amount of grip forces on the wall 708 that are above the threshold force can be used to control the amount of closing (when the grip forces increase) and opening (when grip forces decrease) of jaws on an end effector of a slave device, or can control a different function of an end effector or slave device (e.g., a position of a camera, a magnitude of drill speed, suction, etc.).

Figure 8:
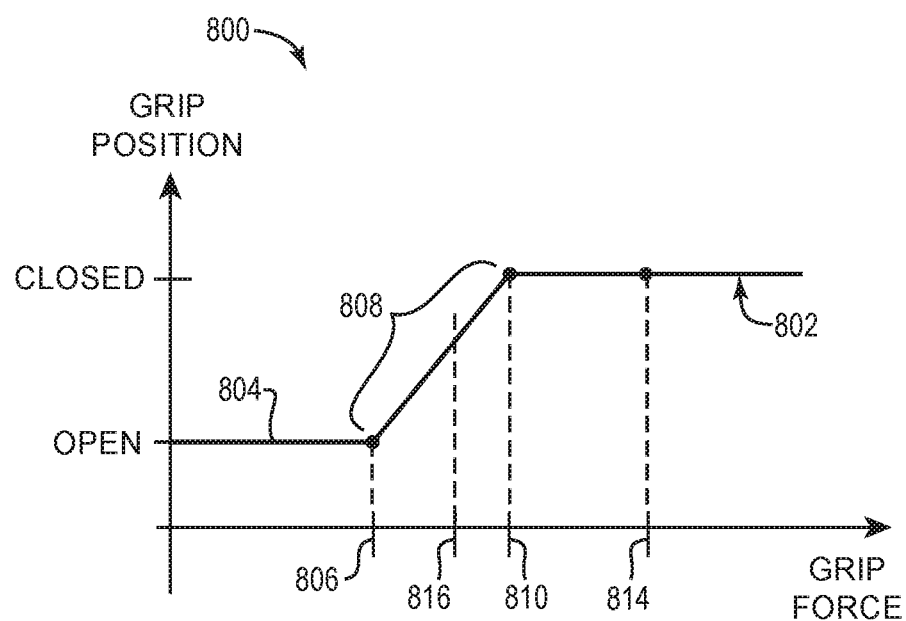
FIG. 8 is a diagrammatic illustration of a graph of example grip forces on the hand controller controlling a grip position of an end effector of a slave device, according to some implementations.

FIG. 8 is a diagrammatic illustration of a graph 800 illustrating an example control scheme for controlling an end effector of a slave device based on grip force on a master control device (hand controller) such as implementations described in FIGS. 2-7 above.

In this example, graph 800 has a vertical axis indicating an example grip position of an end effector, e.g., a range of positions of pinching, grasping, or cutting grip members (e.g., jaws, cutting blades, pincers, etc.) of an end effector, ranging from an open position of the grip members to a closed position of the grip members (e.g., in which the grip members contact each other) as indicated. FIG. 9, described below, shows one example of grip members of an end effector. Graph 800 has a horizontal axis indicating a magnitude of force applied to the hand controller by the fingers of the user, e.g., a pinching or squeezing force on the control grip portion 206 of various implementations described herein, and sensed by one or more force sensors. The horizontal axis may also or alternatively represent pressures or forces sensed by a pressure sensor (or force sensor) of the hand controller based on the grip forces applied by the user to the hand controller.

The curve 802 indicates the relationship between the amount of grip force on the hand controller and the corresponding position of the grip members of the end effector.

As shown in graph 800, an initial grip force can be provided in the force range 804, e.g., when the user is picking up the hand controller or manipulating the controller in space with lower grip forces (e.g., not intending to send grip control signals from the controller). For example, the user can provide a grip force in this force range 804 when changing the position and/or orientation of the controller in space. The force range 804 is not used to output a control signal, e.g., it allows the user to manipulate the controller with a smaller grip force without providing grip commands to the slave device.

The control force threshold 806 (e.g., grip control threshold) indicates the lowest amount of grip force from the user on the hand controller that will cause a control signal to be output to control a grip function of the slave device (e.g., control the end effector). If the grip force from the user is at or greater than (in excess of) the control force threshold 806 and is in a force range 808, the associated grip-controlled function of the slave device is controlled, e.g., in accordance with the magnitude of grip force in the range 808 in some implementations. In some examples, grip members of the end effector are controlled to open or close in accordance with the magnitude of the grip force. For example, a grip force magnitude that increases from the control force threshold 806 within the force range 808 causes the end effector grip members of the slave device to move from their open position toward a closed position. In some implementations, as described above with respect to FIGS. 4-7, control force threshold 806 is at a force magnitude that causes a buckling of ribs in the hand controller, which is perceptible by the user's fingers. In some implementations, the grip-controlled function of the slave device is controlled by sending a grip control signal from the hand controller to the control device, and/or sending a grip control signal from the control device (or hand controller) to the slave device.

If the grip force from the user reduces from a magnitude above the control force threshold to a magnitude below that threshold, then the grip control of the slave device is removed, e.g., no grip control signals are sent to control the end effector or other function of the slave device (position and orientation signals from the position and orientation of the hand controller in space can still be output). In some implementations, grip control signals may still be sent from the hand controller to a control device if the grip force is below the control force threshold, and the control device can refrain from sending grip control signals to the slave device, or can send grip control signals to the slave device that do not cause control of the associated function of the slave device.

At a grip force equal to a maximum control force threshold 810, in some implementations, the grip members of the end effector have been fully closed (e.g., have contacted each other or encountered another physical limit to movement), and no longer move in response to increasing grip force from the user. In some instances, the instrument grip force may increase with greater controller grip force beyond grip force 810. If the user increases grip force past the force threshold 810 which is at a higher force magnitude than the control force threshold 806, the grip members remain in their closed position.

In some implementations, e.g., for some types of end effectors or other functions, a lock force threshold 814 can be provided at a greater force magnitude than the force threshold 810. The lock force threshold 814 can be used to cause the controlled function of the slave device to enter a locked state, e.g., lock the state of the grip members regardless of the user's grip force in a particular range of forces. In some examples, the locked state can be the closed position of the grip members (or close to the closed position when the grip members are holding an object). In some implementations, threshold 814 can also be used to unlock the grip members from a previously-commanded locked state, e.g., enter an unlocked state (examples of which are described below). In some implementations, a different threshold than threshold 814 can be used to command entry to an unlocked state.

In some example implementations, if the slave device function is in an unlocked state, and if the grip force from the user increases from a force magnitude below threshold 814 to a force magnitude at or above (in excess of) threshold 814, a locked state is initiated in which the grip members of the end effector are controlled to be locked in their closed position. While grip members are in the locked state, if the grip force varies within a particular force range, the grip members remain closed (locked) and do not change their positions within their open-close movement range (unlike when in the unlocked state). In various implementations, the particular force range can be, e.g., between threshold 810 and threshold 814, or between a lower force value and threshold 814, where the lower force value is below threshold 810 (e.g., a lower force value of zero force), above threshold 810, etc. In some implementations, the use of the locked state allows the user to reduce the grip force on the hand controller while maintaining the grip members in a closed position, e.g., to hold an object, close a suture, etc., or to otherwise maintain a locked state of a controlled function of the slave device. For example, this locking feature can reduce user fatigue due to maintaining the grip force, reduce unintentional release of grip members by the user's manipulations of the hand controller, and/or allows the user to focus on controller position and orientation instead of controlling or maintaining grip force. In some implementations, a locked state is initiated by sending a lock control signal(s) from the hand controller to the control device, and/or sending a lock control signal(s) from the control device (or hand controller) to the slave device.

If the grip force is reduced substantially below lock force threshold 814, e.g., to a magnitude below an unlock-enable force threshold 816 that is below threshold 810, then an unlock-enabled state is made active in which the locking state is still active but is enabled to be toggled off. If the unlock-enabled state is active, then when the user is ready to remove the locked state (e.g., unlock the grip members), the user applies force having a magnitude at or above a release force threshold, which in this example is the same as the lock force threshold 814. Grip force above the release force threshold, when the unlock-enabled state is active, causes the locked state to be removed, e.g., the locked state is changed to an unlocked state. For example, in the unlocked state after removing the locked state, the grip members again move toward the open position based on a lower grip force according to curve 802 when grip force is in the force range 808. In some implementations, a locked state is released by sending a release/unlock control signal(s) from the hand controller to the control device, and/or sending a release/ unlock control signal(s) from the control device (or hand controller) to the slave device (in some implementations, the unlock control signal can be the same as the lock control signal).

Thus locked and unlocked states of a controlled slave device function (e.g., grip member position) can be toggled using the force threshold 814. In various implementations, different lock and release force thresholds can be used, e.g., a release force threshold can be used that is different than threshold 814 (such as a greater threshold) to remove the locked state, etc.

Other types of functions of the slave device (including other end effector positions or functions) can be controlled using grip forces on a hand controller similarly as described above. For example, other functions can include a magnitude of fluid suction or irrigation, magnitude of grip force, magnitude of energy output, camera functions (magnitude of zoom, panning, etc.), etc. Some slave device functions may not use the locking and releasing features. In some implementations, the lock force threshold 814 and/or release force threshold can be used to lock and release other states besides a closed position, e.g., a different position of a portion of the end effector (e.g., a maximum position in a range of motion, or a middle position between end positions), a magnitude of output (e.g., suction, irrigation, grip force, light, etc.), a setting of a camera (zoom, spatial position, etc.), etc.

FIG. 9 is a perspective view of one example of an end effector 900. For example, end effector 900 can be used as an end effector of an arm assembly of a slave device as referenced with respect to FIGS. 1 and 12. End effector 900 is an example surgical instrument that can operate as forceps in a surgical procedure to grasp tissue, objects, etc. Other types of surgical instruments and end effectors can be used in other implementations as described elsewhere herein.

Figure 12:
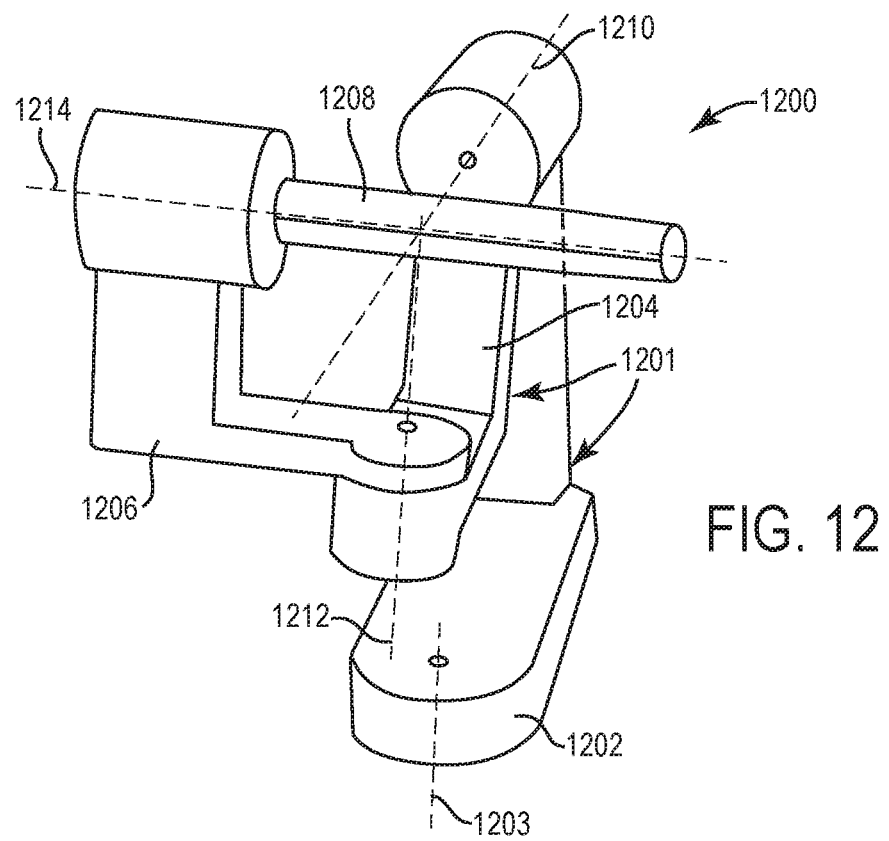
FIG. 12 is a perspective view of an example master control portion that is mechanically grounded and can be engaged by a user.

End effector 900 can be provided at a distal end of a main tube 910 which can be coupled to an arm assembly shown in FIGS. 1 and 12, for example. A proximal clevis 912 is coupled to the distal end of main tube 910, and a distal clevis 914 is coupled to the proximal clevis 912 by a rotational coupling. The forceps end effector 900 includes jaws 916 and 918 that are coupled to the distal clevis 914 by a rotational coupling.

The jaws 916 and 918 are provided with several physical degrees of freedom that can be manipulated by the master controller 122 or 200 (shown in FIGS. 1-7). For example, the jaws 916 and 918 can be rotated about axis 930 of the link between the jaws and the distal clevis 914, e.g., to open and close the jaws with respect to each other as shown by arrow 932, and/or to rotate the jaws in conjunction to a different rotational position. In addition, the jaws 916 and 918 can be rotated about axis 934 of the link between distal clevis 914 and proximal clevis 916, e.g., to rotate the jaws in space. In addition, the jaws 916 and 918 can be translated along linear axis 936.

Movement of the end effector 900 in one or more degrees of freedom can correspond to movement in one or more degrees of freedom of the master controller 122 or 200 by a user. For example, the force applied by a user's fingers to the control grip portion 206 can control corresponding rotational (gripping) positions of the jaws 916 and 918 about axis 930. The motions of the jaws 916 and 918 in other degrees of freedom of the end effector can be controlled by particular associated degrees of freedom of a master controller 122 or 200 in space.

In some implementations, one or more of the degrees of freedom of the end effector 900 can be controlled using tendons, e.g., cables (not shown), that are mechanically coupled to one or more of the elements 914, 916, and 918 and extend through tube 910 to a transmission or other mechanism. For example, the tendons can be coupled to pulleys and/or other transmission elements driven by actuators and sensed by sensors provided in the slave device.

In some examples, the end effector 900 can be inserted through a patient's body wall (or simulated body wall) to reach a surgical site in a surgical procedure. In some implementations, main tube 910 may include a cavity that can provide material transfer along the tube. For example, material may be transferred between a distal end and a proximal end of tube 910, or points near the proximal end and near the distal end of tube 910. For example, main tube 910 (or other tube) can couple a surgical irrigation fluid (liquid or gas) source (not shown) to the end effector 900 so that irrigation fluid can be routed from a source through the main tube to exit via end effector 900. Similarly, main tube 910 can couple a surgical suction source (not shown) to end effector 900 so that material from a surgical site can be drawn into end effector 900 and through tube 910 to the source. Other types of connection features can be provided in other implementations.

Other types of arm assemblies and types of end effectors can be used in other implementations. For example, end effector mechanisms and instruments can include flexible elements, articulated "snake" arms, steerable guide tubes, catheters, scalpels or cutting blades, electro-surgical elements (e.g., monopolar or bipolar electrical instruments), harmonic cutters, scissors, forceps, retractors, dilators, clamps, cauterizing tools, needles, needle drivers, staplers, drills, probes, scopes, light sources, guides, measurement devices, vessel sealers, laparoscopic tools, or other tip, mechanism or device.

Figure 10:
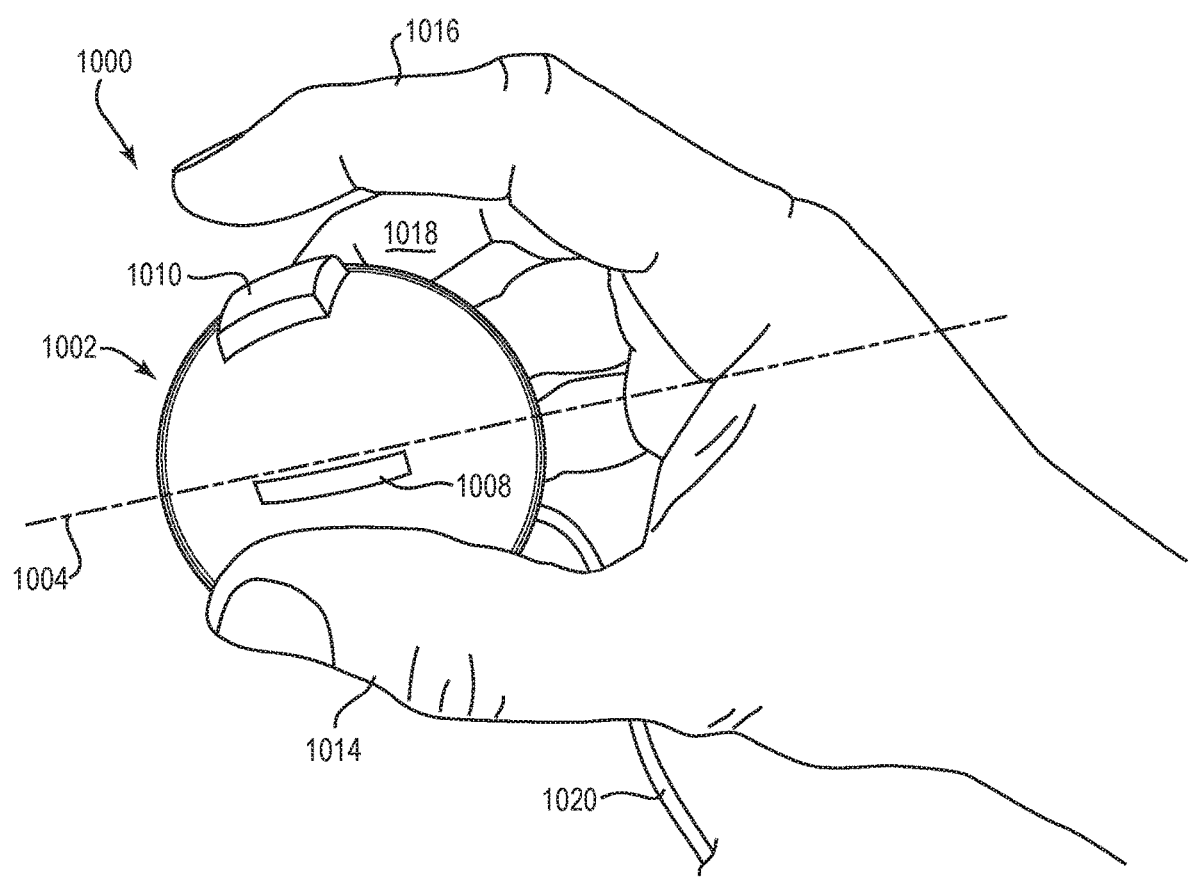
FIG. 10 is a perspective view of another implementation of a master hand controller, according to some implementations.

FIG. 10 is a perspective view of another implementation of a master hand controller 1000 being manipulated by a user's hand, according to some implementations. In this implementation, the hand controller 1000 includes a control body 1002 that is spherical in shape. The position and orientation of the control body 1002 in its workspace can be sensed by one or more types of sensor systems, similarly as described above for the hand controller 200 of FIG. 2. For example, one or more sensor components can be located within the housing interior of the hand controller 1000 to receive and/or transmit sensor signals to allow sensing of the position and/or orientation of the control body 1002. In some implementations, the signals can be received and/or transmitted via a tether, e.g., a cable or wire (described below). In some implementations, wireless signals can be received and/or transmitted via a wireless receiver and/or transmitter, e.g., located within the housing of hand controller 1000.

In some implementations, the hand controller 1000 can have a defined reference axis 1004 which acts as the reference for the orientation of the control body 1002. In some implementations, one or more physical features 1008 can be positioned on the surface of the control body 1002 to assist the user in locating the reference axis 1004 with respect to the orientation of the control body 1002. For example, physical features 1008 can be positioned on opposite sides of the spherical control body 1002 and have a linear shape or orientation that is aligned with or parallel to the reference axis 1004. The user can determine the orientation of the reference axis 1004 by seeing or feeling the orientation of a physical feature 1008. In various examples, the physical feature 1008 can be a bump, ramp, divot, an area with multiple bumps or divots, a rough-textured area, a channel, etc. which allows the user to detect the feature 1008 by touch.

In this example, an actuatable button 1010 is provided as a force sensor to sense an amount of pressure applied by the user and to output a sensor signal to cause a grip control signal to be output by the controller 1000. For example, button 1010 can output a sensor signal indicating the position of the actuating portion of the button 1010 in a degree of freedom of the button, e.g., along an axis of the button approximately perpendicular to the surface of the spherical control body 1002 at the location of the button. The button, in effect, senses the forces applied to its actuatable portion based on the amount of movement of the actuatable portion in response to the force applied by the finger of the user.

In some implementations, button 1010 can be a different type of input control, e.g., any of the force sensors as described with reference to FIG. 2 such as a strain gauge, a pivoting flexure or linkage, a rigid force-sensing element such as a pressure-sensing film or piezoelectric crystal force sensor, etc. A grip control signal provided by the button 1010 can be used similarly to the grip control signal based on the amount of force sensed by the force sensor in the implementations of FIG. 2. For example, the button 1010 can control one or more functions of a slave instrument based on the amount of force (e.g., position of the button in its degree of freedom), e.g., the position of jaws or forceps of an end effector of a slave instrument, an amount of energy, suction, or irrigation applied to a surgical site, etc. An input control similar to button 1010 can be used in other implementations described herein, e.g., on the elongated control body 202 of the controller 200 of FIG. 2.

In this example, the user's thumb 1014 can engage with the physical feature 1008 on the surface of the control body 1002. The user's second finger 1016 can engage with the button 1010 (or other type of input control), and the user's third finger 1018 can engage with a physical feature (not shown) at a location or the side of the control body 1002 that is approximately opposite to the physical feature 1008, e.g., along an axis extending from the first physical feature 1008 to the second physical feature through the control body 1002 and approximately intersecting the central axis 1004. Thus, the input control 1010 can be engaged by a finger of the user that is between two fingers that grasp the control body 1002 at locations on opposite sides of the control body. Other fingers can be used in other use configurations.

In some implementations, the button 1010 (or other input control) can be positioned at a different location on the control body 1002. In some implementations, additional or alternative buttons 1010 (and/or other input controls) can be positioned on the control body 1002 to each provide control signals, e.g., to control associated functions of the slave device. For example, a first button (e.g., button 1010) can be positioned at the location of physical feature 1008 and a second button (e.g., similar to button 1010) can be positioned at a location on the surface of the control body 1002 that is approximately opposite to the first button, e.g., along an axis extending from the first physical feature 1008 to the opposite side through the control body 1002 and approximately intersecting the central axis 1004. Such buttons can thus be grasping controls providing control signals based on the pinching grip of the fingers of the user on opposite sides of the control body 1002. Additional buttons or other input controls can be positioned on the control body 1002 similar to the types of input controls described for the implementations of FIG. 2.

In some implementations, the force-sensing of the button 1010 can be provided by deformable or compressible surfaces of the control body 1002, e.g., using a flexible material for deformable surface(s) and wall(s) of the control body 1002 and/or using the flexible material for particular portions of the surface of the control body 1002. For example, a fluid can be provided within the housing of the control body 1002 and a pressure transducer positioned within the housing can sense the pressure of the fluid forced against the transducer in response to the user squeezing or pinching the control body 1002 on approximately opposite sides of the control body 1002, similarly as described above for FIGS. 2-5. In some implementations, the control body 1002 can include a rigid structure, where the structure includes ribs or other protrusions that support flexible walls of the housing of the control body 1002 from the interior of the control body 1002, similar to the implementations described for FIGS. 4 and 5. For example, a spine can extend parallel to the central axis 1004 to support the ribs, or the ribs can fan out from a central position within the interior of the control body 1002, e.g., at regular angular positions. In some implementations, a spine and/or ribs can make squeezing or deformation preferential about a particular axis of the control body 1002 that is aligned with the spine and/or ribs, e.g., an axis extending through the spine or ribs (such as central axis 204 of implementations described above).

In this example, in some implementations, an extension portion (not shown) can extend from a proximal end of the control body 1002 and, for example, contact the user's hand. Such an extension portion can provide stability and/or an additional element for the user to grasp. For example, in some implementations, such an extension portion may extend toward and engage with the user's palm as described above for extension portion 208, and may include any of the implementations and features described above for extension portion 208.

In various other implementations, the control body 1002 can be other shapes. For example, the control body 1002 can be partially spherical, e.g., having a surface that is hemispherical or having a surface between hemispherical and spherical. In some examples, non-spherical portions of the control body 1002 can have a rectangular, elliptical, or irregularly-shaped cross section. In some implementations, the surface of the control body can form an ellipsoid, super-ellipsoid, or rounded-square shapes, or can be elongated with a square, rectangular, or other polygonal cross-section (with or without rounded corners), etc. Some implementations of control bodies having such shapes may include a spine structure (e.g., ribs and/or spine) similarly as described above.

The implementation shown in FIG. 10 includes an example of a tether connection (e.g., electrical wire or cable) 1020 extending from the control body 1002 at a proximal end of the hand controller 1000 (with respect to the axis 1004). The connection 1020 can be connected to a control system as described above and used to communicate electronic signals to and from the hand controller 1000. In this example, the user can manipulate the hand controller 1000 while the tethered connection 1020 extends out below the user's hand, or can alternatively extend on the side of the user's hand or over the top side of the user's hand. In some implementations, such a proximal end tether can provide advantages similar to those described above with respect to FIG. 3. In some implementations, a tethered connection can be connected and extended from a distal end of the hand controller 1000 (e.g., with respect to axis 1004), similarly as described above.

Figure 11:
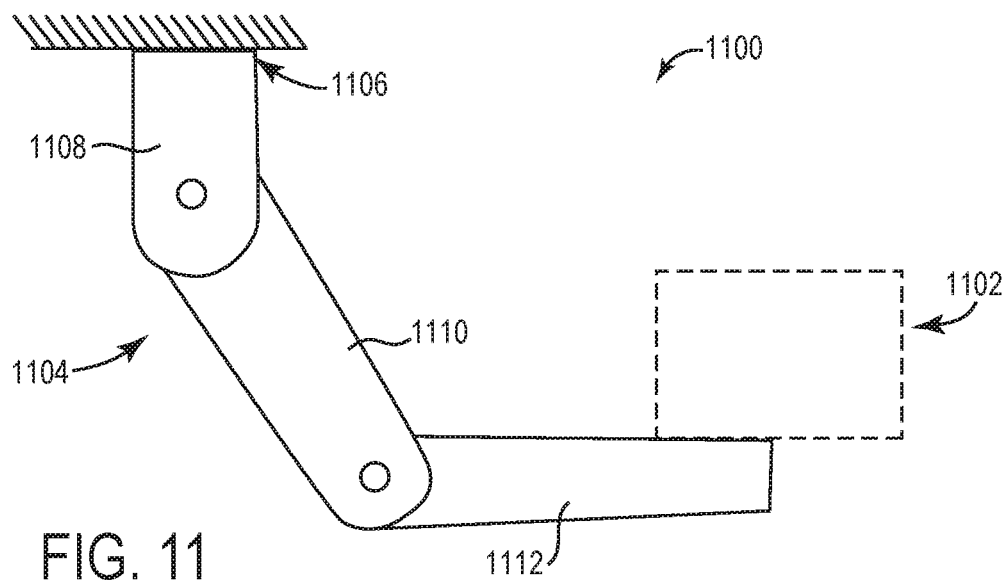
FIG. 11 is a schematic illustration of view of an example controller system that is mechanically grounded.

FIG. 11 is a schematic diagram of an example controller system 1100 that is mechanically grounded, and which can be used with one or more features described herein for a master controller. Controller system 1100 includes a control portion 1102 that can be engaged by a user's hand. The control portion 1102 includes a hand controller portion that can include one or more features described herein, as well as one or more mechanisms. Some examples of control portion 1102 are described in greater detail below with respect to FIG. 12.

Control portion 1102 is coupled to a serial kinematic chain 1104. The proximal end 1106 of the chain 1102 is mechanically grounded. In this example, the kinematic chain 1106 includes three members 1108, 1110, and 1112 that are rotatably coupled to one or more other members of the chain 1106 by rotational couplings having rotational axes. For example, member 1108 is mechanically grounded at a first end 1106 of member 1108 and is rotatably coupled to member 1110 at a second end of member 1108. Member 1110 is rotatably coupled to member 1108 at a first end of member 1110 and rotatably coupled to member 1112 at a second end of member 1110. Member 1112 is rotatably coupled to member 1110 at a first end of member 1112 and coupled (e.g., rotatably coupled) to control portion 1102 at a second end of the member 1112. The rotational axes of the chain 1104 can be sensed and/or driven by sensors and/or actuators. Some implementations can provide additional actuated and/or sensed motion of the kinematic chain, e.g., about axes extending lengthwise through one or more members 1108, 1110, and 1112.

FIG. 12 is a perspective view of an example control portion 1200 that is mechanically grounded and can be engaged by a user. In some examples, control portion 1200 can be the control portion 1102 of the controller system 1100 of FIG. 11. In some implementations, control portion 1200 can be coupled to a different kinematic chain or other structure that is mechanically grounded.

In this example, control portion 1200 includes members of a serial kinematic chain 1201 that includes three members 1202, 1204, and 1206 that are rotatably coupled to one or more other members of the chain 1201 by rotational couplings having rotational axes.

Control portion 1200 can be coupled by a rotational coupling at a first end of member 1202 to the second end of member 1112 of the kinematic chain 1104, allowing rotation about axis 1203 between members 1112 and 1202. Member 1202 is rotatably coupled to member 1204 at a second end of member 1202. Member 1204 is rotatably coupled to member 1202 at a first end of member 1204 and rotatably coupled to member 1206 at a second end of member 1204. Member 1206 is rotatably coupled to member 1204 at a first end of member 1206 and coupled (e.g., rotatably coupled) to a hand controller portion 1208 at a second end of the member 1206. The rotational axes of the chain 1201 can be sensed and/or driven by sensors and actuators.

Hand controller portion 1208 can include features which can be contacted by a user, e.g., a hand of a user. For example, a control body, grips, switches, and/or other features described herein, e.g., with respect to FIGS. 2-8, can be provided on hand controller portion 1208.

In some implementations, the hand controller portion 1208 is coupled at a distal end of a serial kinematic chain that includes members 1206, 1204, 1202, 1112, 1110, and 1108, with the proximal end 1106 of the chain mechanically grounded. This provides a stable platform for the use of the hand controller portion 1208.

In some implementations, the kinematic chain 1201 forms a gimbal mechanism that allows the hand controller portion 1208 to be rotated about the rotational axes of the chain 1201, e.g., axes 1203, 1210, 1212, and 1214. Hand controller portion 1208 can also be translated in at least three linear degrees of freedom allowed by the kinematic chain formed by kinematic chains 1104 and 1201.

Various kinematic chains, linkages, gimbal mechanisms, flexible structures, or combinations of two or more of these can be used with the mechanically grounded hand controller in various implementations to provide one or more degrees of freedom to the hand controller. Some further examples of linkages and/or gimbal mechanisms that can be used with hand controller portion 1208 are described in U.S. Pat. No. 6,714,839 B2, incorporated herein by reference.

Figure 13:
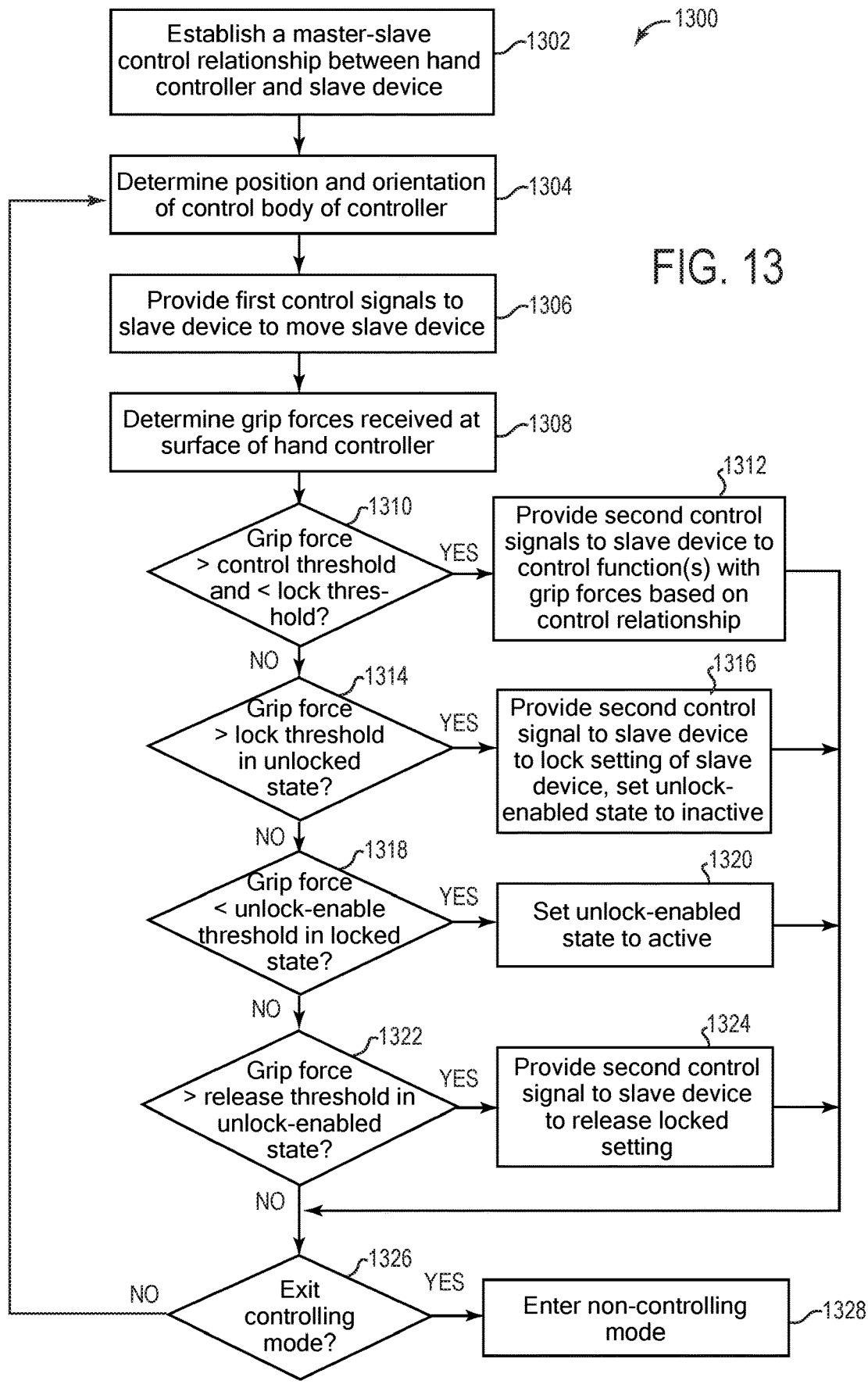
FIG. 13 is a flow diagram illustrating an example method for employing a hand controller including one or more features described herein, according to some implementations.

FIG. 13 is a flow diagram illustrating an example method 1300 for employing a hand controller including one or more features described herein, according to some implementations. Method 1300 can, for example, be used with an example teleoperated system or other control system in which the hand controller is a master controller that controls a slave device. For example, in some implementations, the hand controller is an ungrounded master controller, e.g., master control device 122 of FIG. 1, and method 1300 can be performed by a control circuit component of the master controller 122 or teleoperated system 100, e.g., performed by control system 150. In some implementations, the hand controller is a mechanically grounded master controller. In some examples, the control circuit can include one or more processors, e.g., microprocessors or other control circuits, some examples of which are described below with reference to FIG. 13. In some implementations, states (e.g., locked and unlocked states, control relationships or curves, etc.) and other data used by the method can be stored in one or more storage devices accessible to the control circuit. A single master controller is referred to in method 1300 for explanatory purposes. The master controller can be, for example, any of the controller implementations described herein. Multiple master controllers can be similarly processed as described in method 1300. Other implementations can use a hand controller having one or more features described herein with other types of systems, e.g., non-teleoperated systems, a virtual environment (e.g., medical simulation) implemented on a processing device and having no physical slave device and/or no physical subject interacting with a physical slave device, etc.

In block 1302, a master-slave control relationship is established between a master device (such as an ungrounded hand controller) and a slave device, such as a slave surgical device or instrument in some examples. In some implementations, the master-slave relationship can be established by entering a controlling mode (e.g., following mode) of the hand controller. For example, this control relationship can be established in response to receiving a control signal from the hand controller or a different component of the system that indicates that the hand controller is to enter a controlling mode. In the established control relationship, positions and orientations of the hand controller are sensed as described herein and can be described in signals that are transmitted to a control system, e.g., in the controller, slave device, and/or a separate control system. In some examples, motion of the hand controller in space causes corresponding motion of a controlled instrument of the slave device, and/or can control other functions of the slave device.

Once the control relationship is established in block 1302, the control relationship is maintained in this example method until checked at block 1314. Control actions for the hand controller that are described in this example method include moving the hand controller in its working environment, and applying force to the control body of the hand controller in a pinching or grasping action, described below. Other control actions for the hand controller can be performed, some of which are described elsewhere herein (e.g., activate input controls), and are not described in the blocks of FIG. 13.

In block 1304, the position and orientation of the control body of the hand controller is determined, e.g., by a sensor system. As described herein, the position and orientation of the control body of the hand controller can be sensed using any of a variety of sensor systems, including sensor systems that provide a sensing component (e.g., wireless transmitter) on the hand controller. The position and orientation can be sensed in a working environment (e.g., a working volume within reach of the user) and can reference the central axis of the hand controller, e.g., the longitudinal axis of an elongated hand controller as described for FIGS. 2-3. In some implementations, a control point of the hand controller is determined as a point of the control body that can be indicated to the user using a physical feature on the surface of the control body as described above. The method continues to block 1306.

In block 1306, first control signals are provided to the slave device to, e.g., move the slave device based on the first control signals. The first control signals are based on the position and/or the orientation of the control body in the working environment as determined in block 1304. For example, the slave device can be moved to a slave position and/or orientation based on spatial control signals that indicate the position and/or orientation of the hand controller in the working environment. In some examples, a surgical instrument such as forceps, camera, cutting tool, etc., can be moved based on the movement of the master hand controller, e.g., in a corresponding direction and/or a corresponding distance to the movement of the hand controller in the working environment, and rotated a corresponding amount and/or angle to the rotation of the hand controller in the working environment. In other examples, other operation of the slave device can be changed based on the first control signals. For example, one or more functions of the slave device can be activated based on the first control signals.

In some implementations, a control system (e.g., control system 150 of FIG. 1) or control module can receive sensor signals from a sensor system and/or the hand controller (or other derived signals), which indicate the position and orientation of the hand controller as determined in block 1304. The control system determines the first control signals that are based on the received signals and sends the first control signals to other system components such as the slave device to move the slave device as described above. The method continues to block 1308.

In block 1308, forces (e.g., grip forces) that are received at a surface of the hand controller are determined. The grip forces may be applied to the surface at approximately opposite sides of the hand controller, e.g., by a pinching or grasping of the control body between the fingers of the hand of the user. In various implementations, a force sensor of the hand controller can sense the forces, e.g., based on deformation of compressible surface(s) of the hand controller (e.g., one or more deformable portions of the surface of the hand controller), sensing forces on a force-sensitive rigid surface, etc., and output sensor signals that indicate the amount of received forces.

In some implementations, the hand controller 200 can send the sensor signals to a control system (e.g., control system 150), and the control system can receive the sensor signals or other derived signals. The method continues to block 1310.

In block 1310, it can be determined whether the determined grip force is greater than a control force threshold and less than a lock force threshold (e.g., assuming the controlled slave function is in an unlocked state, which can be a default state in some implementations). In some implementations, similarly as described above for FIG. 8, such force thresholds can be implemented to determine control signal outputs to the slave device. For example, the control force threshold can be used to determine whether the user's grip force has a large enough magnitude to cause control signals to be output to control the slave device. The lock force threshold can be used in some implementations to determine whether the user's grip force has a large enough magnitude to cause control signals to be output to lock a setting of the slave device (in blocks 1314 and 1316 below). If the grip force is not between these thresholds, then the method continues to block 1314, described below.

If the grip force is between the control and lock thresholds in block 1310, then in block 1312, second control signals are provided to the slave device to control one or more functions of the slave device based on a control relationship, e.g., a control curve. The second control signals are based on the amounts of grip forces determined in block 1308, and are based on the control relationship. For example, as shown in the example graph 800 of FIG. 8, the control relationship can be defined with different curves in different force ranges, e.g., a sloped linear curve in force range 808, and a horizontal curve for grip force magnitudes above a maximum control force threshold 810. Other relationships can be used in other implementations, e.g., non-linear curves, etc. In some implementations, the amounts of grip forces are values in a range of force magnitudes that can be sensed on the hand controller, and are converted to a control value within a particular range of values used by the slave device. In some examples, the control value can correspond to a particular position within a range of motion represented by the range of values. For example, an end effector of the slave device, such as a grasping tool or scissors tool, can have jaws that are positioned within their degrees of freedom based on the control values of the second control signals. In other examples, one or more other or additional functions of the slave device can be activated based on the second control signals. For example, the functions can include outputting an amount of energy based on the values of the second control signals from an end effector of the slave device, extending or retracting an end effector component based on the second control signals, etc.

As indicated above, block 1312 is performed assuming that the controlled slave function is in an unlocked state. If it is in a locked state, the controlled slave function is not changed based on the grip forces, e.g., controlled grip members are not moved, etc. The method continues to block 1326, described below.

In block 1314, it can be determined whether the grip force is greater than the lock force threshold and the controlled slave device function is in an unlocked state. In some implementations, similarly as described above for FIG. 8, such force thresholds can be implemented to determine when controlled settings of the slave device are locked and released. For example, the lock force threshold can be used to determine whether the user's grip force has a large enough magnitude to cause a setting of a controlled function of the slave device to be locked, e.g., maintain the setting regardless of user force applied to the hand controller. If the grip force is not between these thresholds, then the method continues to block 1318, described below.

If, in block 1314, the grip force is greater than the lock threshold and the controlled device function is in an unlocked state, then in block 1316, one or more second control signals are provided to the slave device to lock the setting of the controlled function of the slave device such that the setting is maintained (locked) regardless of grip forces received in future iterations that have magnitudes within a particular range of forces. In some examples, the controlled setting can be a particular position of an end effector, e.g., a closed position of grip members as determined by the grip force at the maximum control threshold, or can be a different setting as described above with reference to FIG. 8. In addition, the unlock-enabled state (with reference to blocks 1318 and 1320) can be set to be inactive in block 1316, e.g., so that the controlled slave function cannot be unlocked until the unlock-enabled state is again made active. The method continues to block 1326, described below.

In block 1318, it can be determined whether the grip force is less than an unlock-enable threshold and the controlled device function is in a locked state. For example, the device function may be in a locked state from performing block 1316 in a previous iteration of method 1300. The unlock-enable force threshold can be at a lower force magnitude than the maximum control threshold, as described in the example of FIG. 8. If these conditions do not apply, then the method continues to block 1322, described below.

If the grip force is less than the unlock-enable threshold and the controlled device function is in a locked state, then in block 1320, an unlock-enabled state is set to be active for the controlled device function. This state enables the locked state to be unlocked, e.g., enabled to be toggled off to the unlocked state. The method continues to block 1326, described below.

In block 1322, it can be determined whether the grip force is greater than the release force threshold and whether the controlled device function is in the unlock-enabled state. In some implementations, similarly as described above for FIG. 8, the release force threshold can be used to detect whether the user's grip force has a high enough magnitude to cause control signals to be output to release a locked setting of the slave device, e.g., set an unlocked state, if the unlock-enabled state is active. In various implementations, as described above, the release force threshold is at the same (or about the same) force magnitude as the lock force threshold, or can be at a different force magnitude than the lock force threshold.

If in block 1322 the grip force is not greater than the release force threshold or the unlock-enable threshold is not set, the method continues to block 1326, described below. In some cases when none of the checks of blocks 1310, 1314, 1318, and 1322 are positive, the grip force from the user on the hand controller is below the control force threshold and does not cause second control signals to be output to the slave device, e.g., does not control the controlled slave function. For example, the user may manipulate the hand controller in space without causing second control signals (based on grip forces) to be sent to a control device and/or to the slave device. In some cases when none of these checks are positive, other conditions may apply, e.g., a particular state is not active, etc.

If the grip force is greater than the release force threshold and the unlock-enabled state is active in block 1322, then in block 1324, one or more second control signals are provided to the slave device to release a locked state of a locked setting of the slave device (e.g., make the unlocked state active). This allows the controlled slave function to be adjusted (e.g., a setting of the function can be adjusted) based on grip forces received from the user at the master controller. In some examples, the controlled setting can be a particular position of an end effector of the slave device, e.g., a closed position of end effector grip members that is released to allow the grip members to be moved to any position in their range of motion. In some implementations, a different locked state of a function of the slave device can be released as described above with reference to FIG. 8. The method continues to block 1326, described below.

In some implementations of blocks 1312, 1316, 1320, and/or 1322, a control system (e.g., control system 150 of FIG. 1) or control module can receive sensor signals (or other derived signals), e.g., from the hand controller, which may indicate the forces applied to the surface of the hand controller that are sensed in block 1308. The control system determines the second control signals that are based on these received signals and sends the second control signals to other system components such as the slave device to activate a function of the slave device as described above.

In block 1326, it is determined whether the master-control relationship is ended, e.g., by exiting a controlling mode. In various implementations, controlling mode can be exited in response to the user activating an input control (e.g., a button) of the hand controller, removing fingers from the controller surface, a voice command, other user input, etc. In other examples, controlling mode can be exited in response to a procedure (e.g., surgical procedure) being completed, a condition in the procedure (e.g., an unsafe movement or position of the slave device occurs), etc.

If controlling mode is not exited, the method returns to block 1304 to determine the position and orientation of the hand controller and/or to block 1308 to determine grip forces received at the hand controller. If controlling mode is exited, then in block 1328 the master-slave control relationship is removed or ended, and a non-controlling mode can be entered by the hand controller and control system in which manipulations of the hand controller do not control functions or operations of the slave device. In some implementations, non-controlling mode disables physical or motion control of the slave device or other particular functions based on hand controller manipulations, while enabling some other functions of the slave device (e.g., input to a displayed user interface of the slave device, causing output of audio, etc.). The controlling mode can be again entered similarly as described for block 1302.

The blocks and operations described in the methods disclosed herein can be performed in a different order than shown and/or simultaneously (partially or completely) with other blocks and operations, where appropriate. For example, blocks 1304 and 1308 can be performed at least partially simultaneously to sense multiple inputs from the user using the hand controller, and blocks 1306 and any of blocks 1312, 1316, 1320, and 1324 can be similarly performed at least partially simultaneously. Not all of the described blocks and operations need be performed in various implementations. In some implementations, blocks and operations can be performed multiple times, in a different order, and/or at different times in the methods.

In various implementations, input controls of the hand controller can be manipulated by the user's hand to provide control signals to the control system and/or to the slave device, e.g., at any time during method 1300. As described above, such input controls can include buttons, switches, wheels, etc.

In some additional examples, input controls can provide control signals to provide input to a displayed user interface, virtual environment, or other display provided by a display device, e.g., a user interface displayed on a display device 126 of FIG. 1. In some examples, an input control on the hand controller can be a clutch control, where, for example, moving or activating the input control to one position or state (and/or maintaining the switch at that state) provides a clutch function to enter controlling mode (following mode) with the hand controller. In some implementations, moving or activating the switch to a different position or state can exit the hand controller from controlling mode and cause it to enter non-controlling mode, or cause activation of a different function (e.g., camera control mode in which motion of the hand controller controls a camera of the slave device, a user interface mode in which input from the input controls is provided to a displayed user interface, etc.).

Movement and orientation of the hand controller and activation of input controls are sensed by various sensors as described above, and sensor signals are sent to a control module (e.g., control system 150) in response to the sensing. The hand controller activates one or more selected functions of a plurality of functions provided by a system in communication with the hand controller. For example, a control system 150 or control module can send commands to other system components to activate one or more functions based on the sensor signals received from the hand controller.

The term "function" as used herein can include one or more actions or outputs (including operations or motions) of a controlled device such as a slave device. For example, a surgical slave device may include surgical instruments as described above, and a function can include one instrument action or multiple instrument actions (e.g., actions performed serially and/or at least partially in parallel). In some implementations, a function can be a category of actions performed by a slave instrument. In some examples, a cutting tool such as a knife or a surgical scissors may perform various actions in the category of cutting. In some implementations, the input control activating a function causes one or more actions associated with the activated function to be performed. For example, a cutting function can include one or more actions such as moving a scalpel to create an incision in a surgical site with a straight cut. Alternatively, the cutting function can include actions such as snipping a blood vessel with a surgical scissors, to be cauterized.

Surgical instruments may include cutting tools, grasping tools, cauterizing tools, irrigation tools, suction tools, absorbing tools, etc. In some implementations, the hand controller (or control system) outputs teleoperation control signals based on the sensor signals to control functions including movements of the surgical instruments, and/or mechanical arms holding the surgical instruments, in communication with the hand controller. Various functions can be associated with such controlled instruments or tools, including irrigation (injecting a liquid into or onto a surgical site or other location), suction (removing of such liquid), clutch (disengage control of slave device manipulator arms, e.g., to allow master controllers to be repositioned without such control), turning on or off a camera (capture or record a scene at a physical location such as a surgical site), outputting energy by a cutting tool to cut or seal biological tissue, etc.

Some examples of functions can include, for example, a swap function for a button allowing control of a first telemanipulator arm or instrument to be swapped to a second arm or instrument; a camera function and/or clutch function for a slider switch (e.g., one function for one switch position, the other function for the other switch position); a user interface scroll function for a control wheel allowing scrolling of displayed interface elements (e.g., displayed on a display device); and energy output for surgical instruments mapped to input controls (e.g., control sliders, control rockers, control wheels, control buttons, etc.). In some implementations, particular functions of a teleoperated slave device can be mapped to the activation of finger control(s) of hand controller 200, and such functions can be re-mapped to other functions of the slave device, e.g., based on a different mode of operation, commands received by the slave device, etc.

In some implementations, an input control may be activated by the user (e.g., button pressed) to cause a control signal to be sent and cause activation of a function associated with the input control. In some implementations, the input control is operative to maintain output of the control signal to the system while the input control continues to be activated based on continued user input at the input control (e.g., a button is required to continue to be pressed in order to maintain output of the control signal to the system). In some implementations, the maintained output of the control signal causes the selected function to continue being activated by the system. For example, electrical energy may be applied to perform a coagulate function while an input control button is pressed. In some implementations, an audio signal may be output by the control system to indicate the energy is being applied. In another example, a clutch function and non-controlling mode may be activated and maintained while an input control button is pressed and maintained in pressed state, while controlling mode is active while the button is released. In another example, camera control may be activated as an input control button is continually pressed to allow the hand controller to control camera position and/or orientation, and the button is released (deactivated) to return the hand controller back to controlling the position and/or grip of a surgical grasping instrument and not control the camera position and orientation.

In some implementations, an input control on the hand controller can be used as a toggle to enter or exit control modes. For example, the input control button is pressed and released once to enter camera mode, and is again pressed and released to return to instrument control mode. In another example, the input control can be used to toggle (swap or switch) the arm or instrument being controlled by a hand controller, e.g., switch control to a different manipulator arm (e.g., instrument) on a slave device. In some implementations, the input control may be used to deselect and/or deactivate a function, e.g. using a deselect toggle. In some implementations, the input control can be used as a trigger to initiate a sequence of functions or actions, e.g., a staple sequence of a stapler instrument.

In some implementations, a user interface (UI) and/or status readout can be displayed on one or more display devices of the system (e.g., display screens, virtual reality or augmented reality headsets or goggles, etc.). The user interface can display information related to operation of the hand controller.

In some implementations, actuators can be included in the hand controller to actively output forces on the hand controller, e.g., motors, voice coils, etc. In some examples, such forces can be used to alert the user to particular conditions of the hand controller, of the procedure, etc. For example, a vibration alert can be output by one or more actuators of the hand controller (e.g., a motor rotating an oscillating element), where a vibration force is transmitted to the hand operating the hand controller. In some examples, the vibration alert can be output in response to collisions that have occurred between controlled slave instruments and other objects, in response to a controlled instrument or arm reaching a limit to motion, as a safety alert when using a cutting or energy-outputting instrument, etc. In some implementations, distinct vibration signatures can be provided in association with different respective alerts (e.g., different vibration frequencies and/or amplitudes). Other types of forces can be used for such alerts in some implementations, e.g., single pulses of force, etc.

In some implementations, output such as haptic feedback on the hand controller and/or visual output on a display device can be provided by the system to assist user operation of the teleoperated system. For example, a user interface may display warnings and/or error feedback on a display device, and/or audio output can be provided to indicates such warnings or errors. Such feedback can indicate functions that are potentially dangerous to a patient, and/or that a function to be activated is not appropriate (e.g., according to steps of a stored predetermined procedure) based on previous hand controller movement or previous function(s) activated.

In various implementations, other types of computer-assisted teleoperated systems can be used with one or more hand controller features described herein, in addition to surgical systems. Such teleoperated systems can include controlled slave devices of various forms. For example, submersibles, bomb disposal units, industrial applications, applications in hostile environments and worksites (e.g., due to weather, temperature, pressure, radiation, or other conditions), general robotics applications, and/or remote-control applications (e.g., remote controlled vehicle or device providing a first-person camera view), may utilize teleoperated systems that include slave devices for sensory transmission (conveyed visual, auditory, etc. experience), manipulation of work pieces or other physical tasks, etc., and may use mechanically grounded and/or ungrounded master controllers to remotely control the slave devices. Any such teleoperated systems can be used with the various hand controller features described herein.

Figure 14:
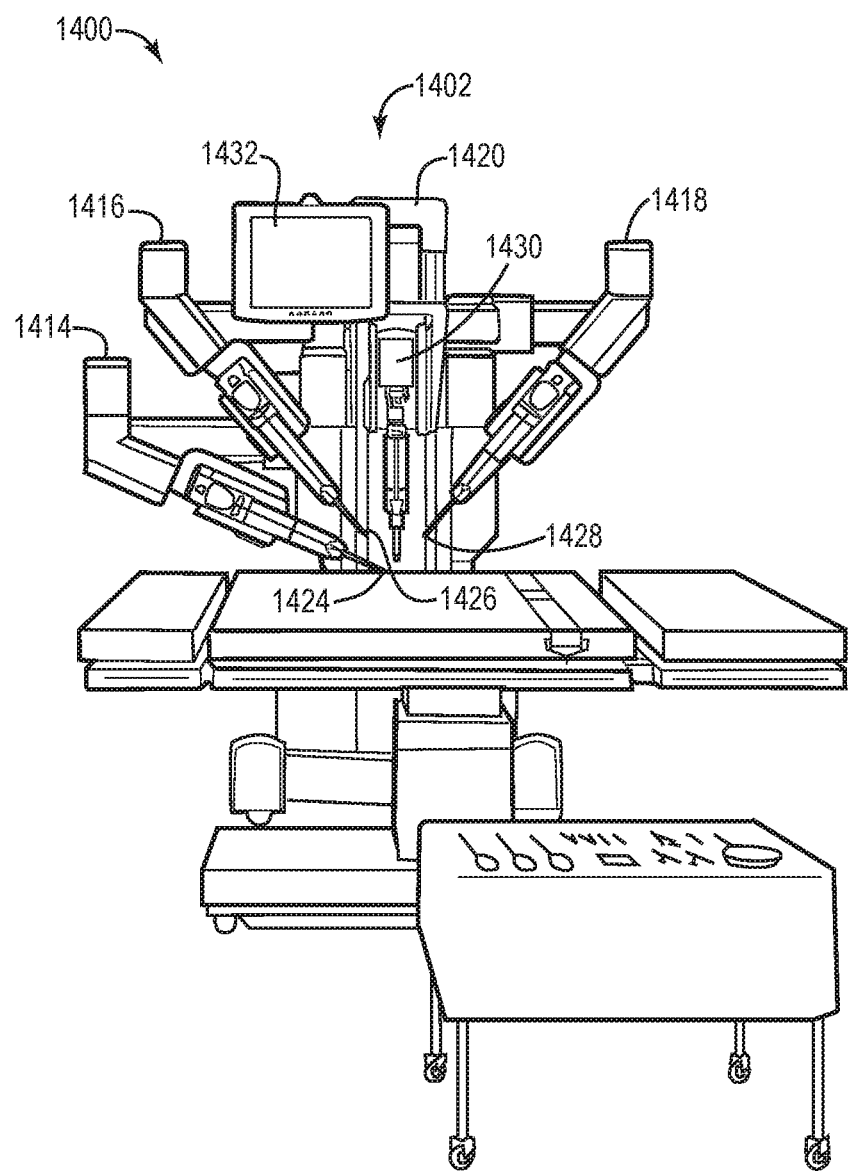
FIG. 14 is a diagrammatic illustration of an example teleoperated slave device and patient site, according to some implementations.

FIG. 14 is a diagrammatic illustration of an example teleoperated slave device and patient site 1400 for an example teleoperated surgical system, which can be used with one or more features disclosed herein according to some implementations.

A manipulator slave device 1402 can be controlled by one or more master controllers of a master control device. For example, one or more master controllers 122 as shown in FIG. 1 (e.g., hand controllers described herein) can be used to control slave device 1402. During a surgical procedure, the slave device can be positioned close to an operating table and patient (or simulated patient) for surgery, where it can remain stationary until a particular surgical procedure or stage of a procedure is completed. Slave device 1402 can include one or more arm assemblies 1414, 1416, and 1418. In some examples, each of these arm assemblies may include a surgical instrument 1424, 1426, and 1428, respectively. Each surgical instrument can include a surgical end effector, e.g., for treating tissue of the patient. An arm assembly 1420 (or other arm assembly 1414, 1416, or 1418) can be configured to hold an image capturing device, e.g., an endoscope 1430, camera, or the like, which can capture images depicting a surgical site or portion thereof. The endoscope can be in communication with to one or more display devices and transmit images to the display devices, such as display device 126 of FIG. 1, a display device 1430 coupled to the slave device, and/or other display devices.

In this example, the arm assemblies may be caused to move and articulate the surgical instruments in response to manipulation of the master controller(s). This enables the user to direct surgical procedures at internal surgical sites through minimally invasive surgical apertures. For example, one or more actuators coupled to the arm assemblies can output force to cause links or other portions of the arm assemblies to move in particular degrees of freedom in response to control signals provided by the master controllers. The master controllers can be used within a room (e.g., an operating room) that also houses the slave device and worksite (e.g., within or outside a sterile surgical field close to an operating table), or can be positioned more remotely from the slave device, e.g., at a different room, building, or other location than the slave device.

Some implementations of the teleoperated system can provide different modes of operation. In some examples, in a non-controlling mode (e.g., safe mode) of the teleoperated system, the controlled motion of manipulator slave device 1402 is disconnected from the master controllers of the workstation in a disconnected configuration, such that movement and other manipulation of the master controls does not cause motion of the manipulator slave device. In a controlling mode of the teleoperated system (e.g., following mode), the motion of the manipulator slave device can be controlled by the master controllers such that movement and other manipulation of the master controllers causes motion of the manipulator slave device, e.g., during a surgical procedure.

In some implementations, the teleoperated surgical system can include a support on which a user, e.g., an operator such as a surgeon, can rest his or her forearms while gripping two grounded master controllers. For example, the master controllers can be positioned in a workspace disposed inwardly toward a patient, beyond the support.

Features disclosed herein may be implemented in various ways, including teleoperated and, if applicable, non-teleoperated (e.g., locally-controlled) implementations. Implementations on da Vinci® Surgical Systems are merely exemplary and are not to be considered as limiting the scope of the features disclosed herein. For example, different types of teleoperated systems having slave devices at worksites can make use of actuated controlled features described herein. Non-teleoperated systems can also use features described herein.

In some implementations, a controlled slave manipulator device can be a simulated device provided as a virtual representation of a device, e.g., presented in a graphical simulation provided by a computing device coupled to the teleoperated system 1400. For example, a user can manipulate hand master controllers and foot controller(s) to control a displayed representation of an end effector in virtual space of the simulation and control virtual functions of the representation (or other virtual instruments) similarly as if the end effector were a physical object coupled to a physical slave device. Such environments can be used for training surgeons in the use of the hand controllers, in some implementations. In some examples, the user can use or manipulate a master controller to control a proxy visual (e.g., a virtual instrument displayed in a virtual displayed environment, and/or a virtual camera or physical camera included on the slave device or other device), and to control teleoperated surgical arms 1414, 1416, 1418, and 1420.

FIG. 15 is a block diagram of an example master-slave system 1500, which can be used for one or more implementations described herein. As shown, system 1500 includes a master device 1502 that a user may manipulate in order to control a slave device 1504 in communication with the master device 1502. More generally, master device block 1502 can include one or more of various types of devices providing one or more controllers that can be physically manipulated by a user. For example, master device 1502 can include a system of one or more master controllers such as one or more master controllers 122 or other hand controllers described herein.

Master device 1502 generates control signals C1 to Cx indicating positions and orientations, states, and/or changes of one or more controllers in their degrees of freedom. For example, the master device 1502 can generate control signals indicating selection of input controls such as physical buttons, hand controller states (e.g., grip control signals), and other manipulations of the hand controller by the user.

A control system 1510 can be included in the master device 1502, in the slave device 1504, or in a separate device, e.g., an intermediary device communicatively connected between master device 1502 and slave device 1504. In some implementations, the control system 1510 can be distributed among multiple of these devices. Control system 1510 receives control signals C1 to Cx and generates actuation signals A1 to Ay, which are sent to slave device 1504. Control system 1510 can also receive sensor signals B1 to By from the slave device 1504 that indicate positions and orientations, states, and/or changes of various slave components (e.g., manipulator arm elements). Control system 1510 can include general components such as a processor 1512, memory 1514, and interface hardware 1516 and 1518 such as a master interface and a slave interface for communication with master device 1502 and slave device 1504, respectively. Processor 1512 can execute program code and control basic operations of the system 1500, and can include one or more processors of various types, including microprocessors, application specific integrated circuits (ASICs), and other electronic circuits. Memory 1514 can store instructions for execution by the processor and can include any suitable processor-readable storage medium, e.g., random access memory (RAM), read-only memory (ROM), Electrical Erasable Read-only Memory (EE-PROM), Flash memory, etc. Various other input and output devices can also be coupled to the control system 1510, e.g., one or more displays 1520.

In this example, control system 1510 includes a mode control module 1540, a controlling mode module 1550, and a non-controlling mode module 1560. Other implementations can use other modules, e.g., a force output control module, sensor input signal module, etc. As used herein, the term "module" can refer to a combination of hardware (e.g., a processor such as an integrated circuit or other circuitry) and software (e.g., machine or processor executable instructions, commands, or code such as firmware, programming, or object code). A combination of hardware and software can include hardware only (i.e., a hardware element with no software elements), software hosted by hardware (e.g., software that is stored at a memory and executed or interpreted by or at a processor), or a combination of hardware and software hosted at hardware. In some implementations, the modules 1540, 1550, and 1560 can be implemented using the processor 1512 and memory 1514, e.g., program instructions stored in memory 1514 and/or other memory or storage devices connected to control system 1510.

Mode control module 1540 can detect when a user initiates a controlling mode and a non-controlling mode of the system, e.g., by user selection of controls, sensing a presence of a user using a master controller, sensing required manipulation of a master controller, etc. The mode control module can set the controlling mode or a non-controlling mode of the control system 1510 based on one or more control signals C1 to Cx. For example, mode control module 1540 may activate controlling mode operation if user detection module detects that a user is in proper position for use of the master controller(s) and that signals (e.g., one or more signals C1 to Cx) indicate the user has contacted the master controller(s). The mode control module 1540 may disable controlling mode if no user touch is detected on the master controller(s) and/or if a user is not in proper position for use of the master controller(s). For example, the mode control module 1540 can inform control system 1510 or send information directly to controlling mode module 1550 to prevent the controlling mode module 1550 from generating actuation signals A1 to An that move slave device 1504.

In some implementations, controlling mode module 1550 may be used to control a controlling mode of control system 1510. Controlling mode module 1550 can receive control signals C1 to Cx and can generate actuation signals A1 to Ay that control actuators of the slave device 1504 and cause it to follow the movement of master device 1502, e.g., so that the movements of slave device 1504 correspond to a mapping of the movements of master device 1502. Controlling mode module 1550 can be implemented using conventional techniques.

In some implementations, controlling mode module 1550 can also be used to control forces on the controller(s) of the master device 1502 as described herein, e.g., forces output on one or more components of the master controllers, e.g., surfaces of a control body, hand grip members (if included), etc., using one or more control signals D1 to Dx output to actuator(s) used to apply forces to the components. For example, one or more of control signals D1 to Dx can be output to one or more actuators configured to output forces to one or more hand controllers, actuators configured to output forces on links coupled to a master controller (if it is a mechanically grounded master controller), etc. In some examples, control signals D1 to Dx can be used to provide haptic feedback, gravity compensation (for mechanically grounded implementations), etc.

In some implementations, a non-controlling mode module 1560 may be used to control a non-controlling mode of system 1500. In the non-controlling mode, user manipulations of master device 1502 have no effect on the movement of one or more components of slave 1504. In some examples, non-controlling mode may be used when a portion of slave 1504, e.g., a slave arm assembly, is not being controlled by master device 1502, but rather is floating in space and may be manually moved. For non-controlling mode, non-controlling mode module 1560 may allow actuator systems in the slave 1504 to be freewheeling or may generate actuation signals A1 to An, for example, to allow motors in an arm to support the expected weight of the arm against gravity, where brakes in the arm are not engaged and permit manual movement of the arm. For example, in a medical procedure, non-controlling mode may allow a side assistant to easily manipulate and reposition an arm or other slave component relative to a patient or directly make some other clinically appropriate adjustment of the arm or slave component.

In some implementations, non-controlling mode can include one or more other operating modes of the control system 1510. For example, a non-controlling mode can be a selection mode in which movement of the master controller in one or more of its degrees of freedom and/or selection of controls of the master controller can control selection of displayed options, e.g., in a graphical user interface displayed by display 1520 and/or other display device. A viewing mode can allow movement of the master controller (s) to control a display provided from imaging devices (e.g. cameras), or movement of imaging devices, that may not be included in the slave device 1504. Control signals C1 to Cx can be used by the non-controlling mode module 1560 to control such elements (e.g., cursor, views, etc.) and control signals D1 to Dx can be determined by the non-controlling mode module to cause output of forces on the master controller(s) during such non-controlling modes, e.g., to indicate to the user interactions or events occurring during such modes.

Implementations described herein may be implemented, at least in part, by computer program instructions or code, which can be executed on a computer. For example, the code may be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general-purpose processors, graphics processors, Application Specific Integrated Circuits (ASICs), and the like.

Note that the functional blocks, operations, features, methods, devices, and systems described in the present disclosure may be integrated or divided into different combinations of systems, devices, and functional blocks as would be known to those skilled in the art.

Although the present implementations have been described in accordance with the examples shown, one of ordinary skill in the art will readily recognize that there can be variations to the implementations and those variations would be within the scope of the present disclosure. Accordingly, many modifications may be made by one of ordinary skill in the art without departing from the scope of the appended claims.

What is claimed is:

1. A control device comprising:
   an elongated control body including a continuous surface;
   a force sensor coupled to the elongated control body, the force sensor configured to sense force applied to the continuous surface of the elongated control body and provide sensor signals in accordance with amounts of the force received on sides of the elongated control body caused by a pinching of the continuous surface of the elongated control body between fingers of a user; and
   a sensor configured to detect at least one of a position or an orientation of the elongated control body in a working environment of the elongated control body.

2. The control device of claim 1, wherein the control device is a surgical system control device configured to provide control signals to a teleoperated surgical system, wherein the sensor signals are used to control positions of a controlled device.

3. The control device of claim 1, wherein:
   the continuous surface of the elongated control body includes deformable portions that are configured to undergo deformation from the force received on the sides of the elongated control body, and
   the force sensor is configured to sense the deformation.

4. The control device of claim 3, further comprising a fluid provided within a housing of the elongated control body, wherein the force sensor includes a transducer configured to detect the deformation of deformable portions of the continuous surface by detecting a change in fluid pressure in response to the deformation.

5. The control device of claim 3, further comprising a rib structure provided within an interior of a housing of the elongated control body, wherein the rib structure is more rigid than the deformable portions of the elongated control body.

6. The control device of claim 5, wherein the rib structure includes ribs provided in a helix centered around a spine shaft that extends along a lengthwise axis of the elongated control body.

7. The control device of claim 5, further comprising a spine shaft extending along a lengthwise axis of the elongated control body,
   wherein:
   the spine shaft is more rigid than a structure of the deformable portions of the elongated control body,
   one or more ribs of the rib structure have a bend in their cross-sectional length from the spine shaft to a wall of the elongated control body, and
   the one or more ribs are configured to buckle in a particular direction in response to the force applied to the continuous surface of the elongated control body meeting a threshold.

8. The control device of claim 3, further comprising a spine shaft extending along a lengthwise axis of the elongated control body, wherein the spine shaft is more rigid than the deformable portions of the elongated control body.

9. The control device of claim 1, wherein the force sensor includes one of:
   a strain gauge, or
   a force-sensing film coupled to the continuous surface of the elongated control body, wherein the force-sensing film receives the force from the fingers of the user.

10. The control device of claim 1, wherein the force sensor includes one or more force-sensitive elements that are positioned to receive the force applied to the continuous surface of the elongated control body, the one or more force-sensitive elements being rigid and opposing deformation of the one or more force-sensitive elements by the force received on opposite sides of the continuous surface of the elongated control body, wherein the one or more force-sensing elements are operable to sense the force applied without deformation and movement of the opposite sides of the continuous surface.

11. The control device of claim 1, further comprising an input control coupled to the elongated control body and configured to output a control signal in response to being activated by a finger of the user.

12. The control device of claim 1, wherein the elongated control body includes a physical feature corresponding to a controller control point, wherein the controller control point corresponds to an instrument control point of a slave instrument controlled by the control device, wherein the instrument control point is an origin pivot point for rotary degrees of freedom of the slave instrument.

13. The control device of claim 1, wherein the elongated control body is mechanically ungrounded.

14. The control device of claim 1, wherein the elongated control body is coupled to a mechanically grounded linkage.

15. A control device comprising:
   a control body configured to engage fingers of a hand of a user, wherein the control body includes a continuous surface that is deformable at a plurality of deformable portions of the continuous surface;
   a force sensor coupled to the control body and configured to sense force applied to the plurality of deformable portions of the continuous surface of the control body from one or more of the fingers of the user, the force causing a deformation of the plurality of deformable portions of the continuous surface, wherein the force sensor is configured to provide sensor signals in accordance with the deformation of the plurality of deformable portions of the continuous surface; and
   at least one sensor configured to detect a position or an orientation of the control body in a working environment of the control body.

16. The control device of claim 15 wherein:
   the control body is elongated and at least partially cylindrical; and
   the force is caused by a pinching of the control body between the fingers.

17. The control device of claim 15 wherein the continuous surface of the control body is spherical.

18. The control device of claim 15, further comprising a fluid provided within a housing of the control body, and wherein the force is configured to detect a change in pressure in the fluid caused by the deformation of the plurality of deformable portions of the continuous surface.

19. A control system comprising:
   a control device comprising:
      an elongated control body including a continuous surface configured to engage fingers of a hand of a user;
      at least one sensor configured to detect a position or an orientation of the elongated control body in a working environment of the elongated control body; and
      a force sensor coupled to the elongated control body, the force sensor configured to sense force applied to the continuous surface of the elongated control body and provide sensor signals in accordance with amounts of the force received on opposite sides of the continuous surface of the elongated control body; and
   a controller coupled to a slave surgical device and in communication with the control device, wherein the controller is configured to provide control signals, including one or more signals derived from the sensor signals, to the slave surgical device while a master-slave control relationship is provided between the control device and the slave surgical device.

20. The control system of claim 19 further comprising a fluid provided within a housing of the elongated control body,
   wherein:
   the continuous surface of the elongated control body includes deformable portions that are configured to undergo deformation from the force received on the opposite sides of the continuous surface of the elongated control body,
   the force sensor is configured to sense the deformation by detecting a change in pressure of the fluid in response to the deformation.

* * * * *

UNITED STATES PATENT AND TRADEMARK OFFICE
CERTIFICATE OF CORRECTION

| | | |
|---|---|---|
| PATENT NO. | : 12,329,487 B2 | Page 1 of 1 |
| APPLICATION NO. | : 17/054109 | |
| DATED | : June 17, 2025 | |
| INVENTOR(S) | : Thompson et al. | |

It is certified that error appears in the above-identified patent and that said Letters Patent is hereby corrected as shown below:

In the Claims

In Column 52, Line 10, delete "the force is" and insert -- the force sensor is -- therefor.

Signed and Sealed this
Twenty-ninth Day of July, 2025

Coke Morgan Stewart
*Acting Director of the United States Patent and Trademark Office*